(12) United States Patent
Pankhurst et al.

(10) Patent No.: US 9,427,396 B2
(45) Date of Patent: Aug. 30, 2016

(54) MAGNETIC MICROBUBBLES, METHODS OF PREPARING THEM AND THEIR USES

(75) Inventors: Quentin Andrew Pankhurst, London (GB); Eleanor Phoebe Jane Stride, London (GB); Colin David Porter, London (GB); Ana García Prieto, London (GB)

(73) Assignee: UCL Business PLC, London (GB)

( * ) Notice: Subject to any disclaimer, the term of this patent is extended or adjusted under 35 U.S.C. 154(b) by 901 days.

(21) Appl. No.: 13/000,841

(22) PCT Filed: Jun. 26, 2009

(86) PCT No.: PCT/GB2009/001614
§ 371 (c)(1),
(2), (4) Date: Apr. 4, 2011

(87) PCT Pub. No.: WO2009/156743
PCT Pub. Date: Dec. 30, 2009

(65) Prior Publication Data
US 2011/0172486 A1    Jul. 14, 2011

(30) Foreign Application Priority Data

Jun. 27, 2008 (GB) .................................. 0811856.4

(51) Int. Cl.
*A61K 9/50* (2006.01)
*A61K 9/00* (2006.01)
*A61K 49/22* (2006.01)

(52) U.S. Cl.
CPC ........... *A61K 9/0009* (2013.01); *A61K 9/5094* (2013.01); *A61K 49/223* (2013.01)

(58) Field of Classification Search
CPC ........... A61K 41/0028; A61K 49/223; A61K 9/0009; A61K 9/5094; A61B 8/481
USPC .......................................................... 600/12
See application file for complete search history.

(56) References Cited

U.S. PATENT DOCUMENTS

| 4,652,257 A | 3/1987 | Chang |
| 4,832,941 A | 5/1989 | Berwing et al. |

(Continued)

FOREIGN PATENT DOCUMENTS

| AR | 001496 A1 | 10/1997 |
| CA | 2154867 A1 | 6/1995 |

(Continued)

OTHER PUBLICATIONS

Coussios, et al., Role of Acoustic Cavitation in the Delivery and Monitoring of Cancer Treatment by High-Intensity Focused Ultrasound (HIFU), Int. J. Hyperthermia, 2007, 23(2):105-120.

(Continued)

*Primary Examiner* — Charles A Marmor, II
*Assistant Examiner* — Thaddeus Cox
(74) *Attorney, Agent, or Firm* — Quarles & Brady LLP

(57) ABSTRACT

The invention provides a method of preparing a suspension of microbubbles for use in a carrier liquid, wherein the microbubbles have a gas core and a liquid shell, said liquid shell comprising magnetic nanoparticles, and wherein the microbubbles satisfy the following conditions: (i) the force due to buoyancy ($F_{BW}$) of the microbubble in the carrier liquid is greater than the weight (W) of the microbubble; (ii) the magnetic force ($F_M$) on the microbubble due to a magnetic field applied to the carrier liquid is greater than the combined weight (W) and force due to buoyancy ($F_{BW}$) of the microbubble; (iii) said magnetic force ($F_M$) on the microbubble is greater than the force due to viscous drag ($F_D$) on the microbubble due to flow of the carrier liquid; and (iv) the scattering cross section ($\sigma_{scat}$) of the microbubble to ultrasound allows the microbubble to be detectable and rupturable on exposure to ultrasound.

23 Clams, 14 Drawing Sheets

(56) References Cited

U.S. PATENT DOCUMENTS

| | | | |
|---|---|---|---|
| 4,844,882 A | 7/1989 | Widder et al. | |
| 5,123,414 A | 6/1992 | Unger | |
| 5,149,319 A | 9/1992 | Unger | |
| 5,209,720 A | 5/1993 | Unger | |
| 5,215,680 A | 6/1993 | D'Arrigo | |
| 5,230,882 A | 7/1993 | Unger | |
| 5,271,928 A | 12/1993 | Schneider et al. | |
| 5,310,540 A | 5/1994 | Giddey et al. | |
| 5,348,016 A | 9/1994 | Unger et al. | |
| 5,370,901 A | 12/1994 | Tournier et al. | |
| 5,380,519 A | 1/1995 | Schneider et al. | |
| 5,411,730 A | 5/1995 | Kirpotin et al. | |
| 5,413,774 A | 5/1995 | Schneider et al. | |
| 5,420,176 A | 5/1995 | Unger et al. | |
| 5,531,980 A | 7/1996 | Schneider et al. | |
| 5,556,610 A | 9/1996 | Yan et al. | |
| 5,558,092 A | 9/1996 | Unger et al. | |
| 5,562,893 A | 10/1996 | Lohrmann | |
| 5,567,414 A | 10/1996 | Schneider et al. | |
| 5,578,292 A | 11/1996 | Schneider et al. | |
| 5,580,575 A | 12/1996 | Unger et al. | |
| 5,605,673 A | 2/1997 | Schutt et al. | |
| 5,643,553 A | 7/1997 | Schneider et al. | |
| 5,658,551 A | 8/1997 | Schneider et al. | |
| 5,698,397 A | 12/1997 | Zarling et al. | |
| 5,705,187 A | 1/1998 | Unger | |
| 5,711,933 A | 1/1998 | Bichon et al. | |
| 5,827,504 A | 10/1998 | Yan et al. | |
| 5,840,275 A | 11/1998 | Bichon et al. | |
| 5,846,517 A | 12/1998 | Unger | |
| 5,846,518 A | 12/1998 | Yan et al. | |
| 5,863,520 A | 1/1999 | Bichon et al. | |
| 5,876,683 A | 3/1999 | Glumac et al. | |
| 5,897,851 A | 4/1999 | Quay et al. | |
| 5,911,972 A | 6/1999 | Schneider et al. | |
| 5,976,501 A | 11/1999 | Jablonski | |
| 5,997,898 A | 12/1999 | Unger | |
| 6,042,809 A | 3/2000 | Tournier et al. | |
| 6,051,207 A | 4/2000 | Klaveness et al. | |
| 6,110,443 A | 8/2000 | Schneider et al. | |
| 6,123,922 A | 9/2000 | Bichon et al. | |
| 6,136,293 A | 10/2000 | Schneider et al. | |
| 6,139,818 A | 10/2000 | Bichon et al. | |
| 6,177,061 B1 | 1/2001 | Klaveness et al. | |
| 6,183,725 B1 | 2/2001 | Yan et al. | |
| 6,200,548 B1 | 3/2001 | Bichon et al. | |
| 6,333,021 B1 | 12/2001 | Schneider et al. | |
| 6,414,139 B1 | 7/2002 | Unger et al. | |
| 6,485,705 B1 | 11/2002 | Schneider et al. | |
| 6,509,004 B1 | 1/2003 | Henriksen et al. | |
| 6,548,048 B1 | 4/2003 | Cuthbertson et al. | |
| 6,585,955 B1 | 7/2003 | Schneider et al. | |
| 6,592,846 B1 | 7/2003 | Schneider et al. | |
| 6,595,925 B1 | 7/2003 | Ostensen et al. | |
| 6,599,234 B1 | 7/2003 | Gray et al. | |
| 6,610,547 B1 | 8/2003 | Klaveness et al. | |
| 6,613,306 B1 | 9/2003 | Schneider et al. | |
| 7,033,574 B1 | 4/2006 | Schneider et al. | |
| 2001/0001279 A1 | 5/2001 | Schneider et al. | |
| 2001/0002275 A1 | 5/2001 | Oldenburg et al. | |
| 2001/0002993 A1 | 6/2001 | Ostensen et al. | |
| 2001/0010811 A1 | 8/2001 | Dugstad et al. | |
| 2001/0022963 A1 | 9/2001 | Klaveness et al. | |
| 2001/0051131 A1 | 12/2001 | Unger | |
| 2001/0053355 A1 | 12/2001 | Edelson | |
| 2001/0053384 A1 | 12/2001 | Greenleaf et al. | |
| 2002/0010412 A1 | 1/2002 | Eppstein | |
| 2002/0044909 A1 | 4/2002 | Achilefu et al. | |
| 2002/0054852 A1 | 5/2002 | Cate | |
| 2002/0065467 A1 | 5/2002 | Schutt | |
| 2002/0106328 A1 | 8/2002 | Johnson et al. | |
| 2002/0147136 A1 | 10/2002 | Von Wronski et al. | |
| 2002/0150538 A1 | 10/2002 | Schneider et al. | |
| 2002/0156117 A1 | 10/2002 | Achilefu et al. | |
| 2002/0159951 A1 | 10/2002 | Unger et al. | |
| 2002/0159952 A1* | 10/2002 | Unger | 424/9.51 |
| 2002/0172643 A1 | 11/2002 | Klaveness et al. | |
| 2002/0197211 A1 | 12/2002 | Henriksen et al. | |
| 2003/0017109 A1 | 1/2003 | Schneider et al. | |
| 2003/0039613 A1 | 2/2003 | Unger | |
| 2003/0039777 A1 | 2/2003 | Dalton et al. | |
| 2003/0059373 A1 | 3/2003 | Klaveness et al. | |
| 2003/0064027 A1 | 4/2003 | Schneider et al. | |
| 2003/0104359 A1 | 6/2003 | Cuthbertson et al. | |
| 2003/0147812 A1 | 8/2003 | Ueberle | |
| 2003/0175211 A1 | 9/2003 | Schneider et al. | |
| 2003/0185759 A1 | 10/2003 | Schneider et al. | |
| 2003/0194376 A1 | 10/2003 | Schneider et al. | |
| 2003/0206863 A1 | 11/2003 | Quay | |
| 2003/0215393 A1 | 11/2003 | Short | |
| 2003/0216638 A1* | 11/2003 | Dharmakumar et al. | 600/420 |
| 2003/0228411 A1 | 12/2003 | Tai et al. | |
| 2004/0018974 A1 | 1/2004 | Arbogast et al. | |
| 2004/0063669 A1 | 4/2004 | Fischer et al. | |
| 2004/0086572 A1 | 5/2004 | Dailey et al. | |
| 2004/0126322 A1 | 7/2004 | Bichon et al. | |
| 2004/0170564 A1 | 9/2004 | Skurtveit et al. | |
| 2004/0197269 A1 | 10/2004 | Yan et al. | |
| 2004/0208826 A1 | 10/2004 | Schneider et al. | |
| 2004/0230122 A1 | 11/2004 | Eriksen et al. | |
| 2004/0253184 A1 | 12/2004 | Li et al. | |
| 2005/0013780 A1 | 1/2005 | Otoboni et al. | |
| 2005/0053552 A1 | 3/2005 | Quay | |
| 2005/0074506 A1 | 4/2005 | Natan et al. | |
| 2005/0089470 A1 | 4/2005 | Johnson et al. | |
| 2005/0089471 A1 | 4/2005 | Johnson et al. | |
| 2005/0100963 A1 | 5/2005 | Sato et al. | |
| 2005/0123454 A1 | 6/2005 | Cox | |
| 2005/0163716 A1 | 7/2005 | Unger et al. | |
| 2005/0175702 A1 | 8/2005 | Muller-Schulte | |
| 2005/0175709 A1* | 8/2005 | Baty et al. | 424/489 |
| 2005/0207980 A1 | 9/2005 | Schneider et al. | |
| 2005/0283098 A1* | 12/2005 | Conston et al. | 601/2 |
| 2006/0024232 A1 | 2/2006 | Schnitzer et al. | |
| 2006/0024756 A1 | 2/2006 | Tibbe et al. | |
| 2006/0034761 A1 | 2/2006 | Syud et al. | |
| 2006/0034770 A1 | 2/2006 | Schneider et al. | |
| 2006/0034771 A1 | 2/2006 | Schneider et al. | |
| 2006/0049116 A1 | 3/2006 | Subramanian | |
| 2006/0060464 A1 | 3/2006 | Chang | |
| 2006/0099145 A1 | 5/2006 | Takeyama | |
| 2006/0171894 A1 | 8/2006 | Takeyama | |
| 2008/0063603 A1* | 3/2008 | Schneider et al. | 424/9.52 |
| 2010/0227279 A1* | 9/2010 | True | 430/322 |

FOREIGN PATENT DOCUMENTS

| | | |
|---|---|---|
| CA | 2218860 C | 1/1997 |
| CA | 2428896 A1 | 11/2003 |
| CN | 1523076 A | 8/2004 |
| CN | 1667413 A | 9/2005 |
| CN | 1718619 A | 1/2006 |
| CN | 1857728 A | 11/2006 |
| DE | 4412651 A1 | 10/1995 |
| DE | 10040380 A1 | 2/2002 |
| DE | 102004036780 A1 | 3/2006 |
| EP | 0042249 A2 | 12/1981 |
| EP | 0458745 A1 | 11/1991 |
| EP | 0554213 A1 | 8/1993 |
| EP | 1252885 A2 | 10/2002 |
| EP | 1588699 A2 | 10/2005 |
| GB | 2340225 A | 2/2000 |
| JP | 7241192 A | 9/1995 |
| JP | 8272136 A | 10/1996 |
| JP | 11071265 A | 3/1999 |
| JP | 2000319165 A | 11/2000 |
| JP | 2006045132 A | 2/2006 |
| JP | 2006045238 A | 2/2006 |
| JP | 2006192285 A | 7/2006 |
| JP | 2006315174 A | 11/2006 |
| RU | 2138293 C1 | 9/1999 |
| WO | 9222247 A1 | 12/1992 |
| WO | 9516467 A1 | 6/1995 |
| WO | 9618421 A1 | 6/1996 |

(56) References Cited

FOREIGN PATENT DOCUMENTS

| | | |
|---|---|---|
| WO | 9628090 | 9/1996 |
| WO | 9628090 A1 | 9/1996 |
| WO | 9640281 A2 | 12/1996 |
| WO | 9823298 A1 | 6/1998 |
| WO | 9952505 A1 | 10/1999 |
| WO | 9959556 A1 | 11/1999 |
| WO | 0112071 A1 | 2/2001 |
| WO | 03034975 A2 | 5/2003 |
| WO | 03069412 A1 | 8/2003 |
| WO | 2004032970 A2 | 4/2004 |
| WO | 2004071535 A1 | 8/2004 |
| WO | 2004110279 A1 | 12/2004 |
| WO | 2005022667 A2 | 3/2005 |
| WO | 2005023406 A2 | 3/2005 |
| WO | 2005025508 A2 | 3/2005 |
| WO | 2005063306 A1 | 7/2005 |
| WO | 2005070299 A1 | 8/2005 |
| WO | 2005079843 A1 | 9/2005 |
| WO | 2005086639 A2 | 9/2005 |
| WO | 2006018433 A1 | 2/2006 |
| WO | 2006037803 A1 | 4/2006 |
| WO | 2006064451 A2 | 6/2006 |
| WO | 2006064453 A2 | 6/2006 |
| WO | 2006069677 A2 | 7/2006 |
| WO | 2006094951 A1 | 9/2006 |
| WO | 2006102395 A2 | 9/2006 |
| WO | 2006122414 A1 | 11/2006 |
| WO | 2007008220 A2 | 1/2007 |
| WO | 2007012209 A1 | 2/2007 |
| WO | 2007015179 A1 | 2/2007 |
| WO | 2007028981 A1 | 3/2007 |
| WO | 2007028984 A1 | 3/2007 |
| WO | 2007047149 A2 | 4/2007 |

OTHER PUBLICATIONS

Dharmakumar, et al., A Novel Microbubble Construct for Intracardiac or Intravascular MR Manometry: A Theoretical Study, Phys. Med. Biol., 2005, 50:4745-4762.

Klibanov, Ligand-Carrying Gas-Filled Microbubbles: Ultrasound Contrast Agents for Targeted Molecular Imaging, Bioconjugate Chem., 2005, 16:9-17.

Lindner, et al., Targeting Inflammation, Biomedical Aspects of Drug Targeting, 2002, pp. 149-172, Kluwer, Boston.

Lindner, Microbubbles in Medical Imaging: Current Applications and Future Directions, Nature Reviews Drug Discovery, 2004, 3:527-532.

McCulloch, et al., Ultrasound Contrast Physics: A Series on Contrast Echocardiography, Article 3, J. Am. Soc. Echocardioigr., 2000, 13:959-967.

Mykhaylyk, et al., Magnetic Nanoparticle Formulations for DNA and siRNA Delivery, Journal of Magnetism and Magnetic Materials, 2007, 311:275-281.

Newman, et al., Ultrasound Gene Therapy: On the Road from Concept to Reality, Echocardiography, 2001, 18:339-347.

Plank, et al., The Magnetofection Method: Using Magnetic Force to Enhance Gene Delivery, Biol. Chem., 2003, 384:737-747.

Plank, et al., Localized Nucleic Acid Delivery Using Magnetic Nanoparticles, European Cells and Materials, 2005, 10 (Suppl 5):8.

Rahim, et al., Physical Parameters Affecting Ultrasound/Microbubble-Mediated Gene Delivery Efficiency In Vitro, Ultrasound in Med. & Biol., 2006, 32(8):1269-1279.

Soetanto, et al., Development of Magnetic Microbubbles for Drug Delivery System (DDS), Jpn. J. Appl. Phys., 2000, 39:3230-3232.

Soetanto, et al., Ferromagnetic Ultrasound Microbubbles Contrast Agent, Proceedings of the 25th Annual International Conference of the IEEE EMBS, Cancun, Mexico, Sep. 17-21, 2003, pp. 1226-1229.

Stride, et al., Investigating the Significance of Multiple Scattering in Ultrasound Contrast Agent Particle Populations, IEEE Transactions on Ultrasonics, Ferroelectrics, and Frequency Control, 2005, 52(12):2332-2345.

Stride, The Influence of Surface Adsorption on Microbubble Dynamics, Phil. Trans. R. Soc. A, 2008, 366:2103-2115.

Takalkar, et al., Binding and Detachment Dynamics of Microbubbles Targeted to P-selectin Under Controlled Shear Flow, Journal of Controlled Release, 2004, 96:473-482.

Unger, et al., Gene Delivery Using Ultrasound Contrast Agents, Echocardiography, 2001, 18(4):355-361.

Vlaskou, et al., Magnetic Microbubbles: New Carriers for Localized Gene and Drug Delivery, Molecular Therapy, 2006, 13(Suppl 1):S290.

UK Intellectual Property Office, Search Report, GB0811856.4, Oct. 28, 2008.

International Search Report, PCT/GB2009/001614, May 28, 2010.

European Patent Office, Examination Report, EP09769584.5, Sep. 5, 2011.

International Search Report, May 28, 2010.

Soetanto, Kawan et al., Development of Magnetic Microbubbles for Drug Delivery System (DDS), Jpn. J. Appl. Phys., 2000, 39(5B): 3230-3232.

Plank, C. et al., Localized Nucleic Acid Delivery Using Magnetic nanoparticles, European Cells and Materials, 2005, 10: 8.

Vlaskou et al., Magnetic Microbubbles: New Carriers for Localized Gene and Drug Delivery, Molecular Therapy, 2006, 13: S290.

* cited by examiner

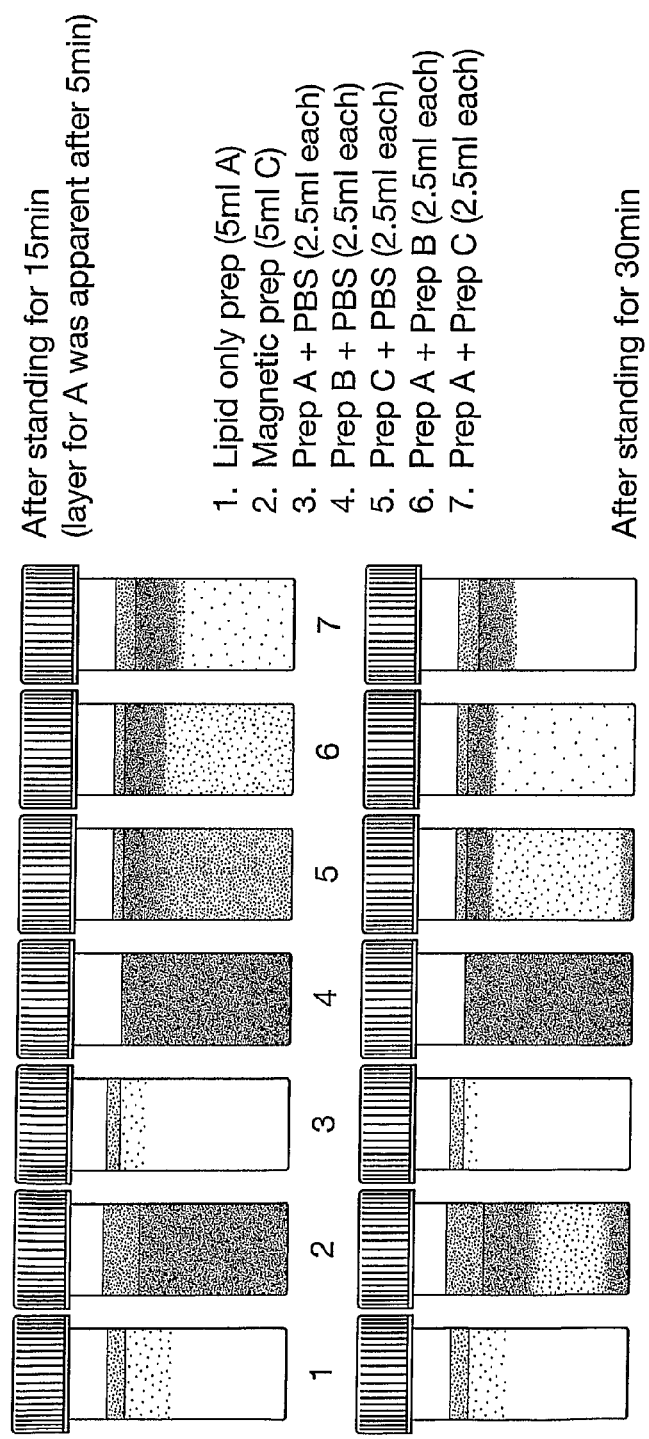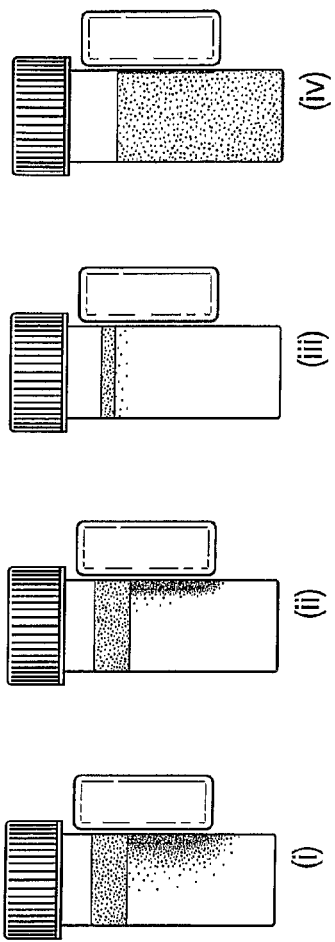
Fig.6.
Fig.7.

Neither Field

Ultrasound Only

Magnetic Field Only

Ultrasound +Magnetic Field

MAGNETIC MICROBUBBLES, METHODS OF PREPARING THEM AND THEIR USES

CROSS-REFERENCE TO RELATED APPLICATIONS

This application claims priority to PCT International Application No. PCT/GB2009/001614 filed on Jun. 26, 2009, which claims priority to UK Patent Application No. 0811856.4 filed Jun. 27, 2008, both of which are incorporated herein by reference.

The invention relates to a method of preparing a suspension of microbubbles, where the structural parameters of the microbubbles in the suspension have been optimised for use in a method for the targeted delivery of a therapeutic agent involving magnetic actuation of the microbubbles and ultrasound exposure to rupture the microbubbles. The invention is also concerned with the magnetic microbubbles themselves and their uses, as well as methods and a computer program for determining an optimised microbubble design.

Gas microbubbles, coated with a surfactant or polymer shell, have become established as an effective type of contrast agent available for diagnostic ultrasound imaging. The gas core of the microbubbles scatters ultrasound both more efficiently and over a wider range of frequencies than biological cells, producing strong contrast between the vasculature and the surrounding tissue.

More recently, the possibility of using microbubbles in the targeted delivery of a drug or therapeutic agent to a specific organ or tissue has been recognised. Therapeutic agents may be incorporated into the encapsulating shell of the microbubbles. The microbubbles can then be introduced into the body intravenously and their passage through the bloodstream can be traced using low intensity ultrasound. Once the microbubbles have found their way naturally (i.e. through being carried by the blood) to their intended location, the therapeutic agent can be released by focusing and increasing the intensity of the ultrasound to selectively rupture the microbubbles at the site for treatment. It has been shown that the rupture of the microbubbles may also enhance the cellular uptake of the therapeutic agent or drug by temporarily increasing the membrane permeability of nearby cells (Rahim et al; Ultrasound Med. Biol., 2006; 32(8): 1269-79). This effect is known as sonoporation.

A limitation of this approach is that the microbubbles do not dwell for sufficient periods of time at the site targeted for treatment. One way of overcoming this problem is to incorporate a magnetic material in the microbubble. An applied magnetic field may then be used to actuate the microbubbles toward the site of interest and to increase their dwell time there.

Several research groups have described the preparation of magnetic, gas-filled microbubbles. U.S. Pat. No. 5,215,680 (D'Arrigo) describes the preparation of gas-filled, lipid coated microbubbles having a paramagnetic label. These microbubbles are contrast agents that can be used in both ultrasound imaging and magnetic resonance (MR) imaging methods. Planck et al. (European Cells and Materials, 2005; 10 (Suppl. 5), 8) and Soetanto et al. (Jpn. J. Appl. Phys., 2000; 39(5B), 3230-3232) have each described methods for the preparation of magnetic microbubbles. They also mention their potential for use as a drug delivery system. None of these reports, however, demonstrate that it is possible to deliver a therapeutic agent by magnetic actuation of the microbubbles followed by ultrasound exposure, nor that there is any improvement in the amount of therapeutic agent delivered to the target site compared to non-magnetic microbubbles. It is not clear if the magnetic microbubbles described in these documents are capable of being used in a targeted method of delivering a therapeutic agent.

US 2003/0216638 (Dharmakumar et al.) describes gas-filled, magnetic microbubbles for use in a sensitivity enhanced manometry method to determine intravascular or intercardiac pressure. A number of magnetic microbubble formulations had been described prior to US 2003/0216638, but in practice they generally suffered from inadequate magnetic sensitivity and were not suitable for use in an in vitro MR manometry method. US 2003/0216638 shows that the microbubble must possess certain characteristics for it to be useable in practice in MR manometry methods.

SUMMARY OF THE INVENTION

The inventors have shown that there is a range of optimised microbubble structures for use in the delivery of a therapeutic agent to a target site, where the magnetic field for actuating the microbubble, the ultrasound frequency for rupturing the microbubble, and the flow velocity of the liquid into which the microbubbles are to be introduced are known (from measurement or from the apparatus that is used to apply the magnetic field or ultrasound). It has been demonstrated that magnetic microbubbles prepared according to the optimised microbubble design show improved cell transfection compared to non-magnetic microbubbles. Moreover, the optimised magnetic microbubble formulations show improved cell transfection compared to magnetic microbubble formulations that do not fulfil the requirements of the optimised microbubble design.

According to a first aspect of the invention there is provided a method of preparing a suspension of microbubbles for use in a carrier liquid, wherein the microbubbles have a gas core and a liquid shell, said liquid shell comprising magnetic nanoparticles, and wherein the method comprises the steps of:

(a) determining a size of the shell relative to the gas core and an amount of nanoparticles in the shell of a microbubble that satisfy the following conditions:

the force due to buoyancy ($F_{BW}$) of the microbubble in the carrier liquid is greater than the weight (W) of the microbubble;

(ii) the magnetic force ($F_M$) on the microbubble due to a magnetic field applied to the carrier liquid is greater than the combined weight (W) and force due to buoyancy ($F_{BW}$) of the microbubble;

(iii) said magnetic force ($F_M$) on the microbubble is greater than the force due to viscous drag ($F_D$) on the microbubble due to flow of the carrier liquid; and (iv) the scattering cross section ($\sigma_{scat}$) of the microbubble to ultrasound allows the microbubble to be detectable and rupturable on exposure to ultrasound;

(b) using the amount of nanoparticles in the shell and the relative size of the shell to the gas core of the microbubble to determine the amount of magnetic nanoparticles and the amount of liquid for the shell needed to prepare a suspension of the microbubbles; and (c) preparing a suspension of the microbubbles using the amount of magnetic nanoparticles and the amount of liquid for the shell needed to prepare the suspension.

The invention also relates to a method of determining for a microbubble for use in a carrier liquid, which microbubble has a gas core and a liquid shell, said liquid shell comprising magnetic nanoparticles, a size of the shell relative to the gas core and an amount of nanoparticles in the shell for a microbubble by applying the conditions (i) to (iv) set out above, and, optionally, any further conditions set out below.

The amount of nanoparticles in the shell may be determined in terms of their percentage by weight or volume of the shell, their concentration in the shell, their molar percentage of the shell, their volume fraction α of the shell or any other appropriate amount for expressing the amount of nanoparticles in the shell of the microbubble. Preferably, the amount of nanoparticles in the shell of the microbubble is determined as a volume fraction α of the magnetic nanoparticles suspended in the shell.

The amount of magnetic nanoparticles in the shell must be sufficient to allow the magnetic force ($F_M$) to satisfy the conditions set out in (i) and (ii) above. However, there is an upper limit for the amount of nanoparticles present in the shell, which is determined by practical considerations. Preferably, the volume fraction α of the magnetic nanoparticles in the shell satisfies the further condition that $0<\alpha<0.2$. More preferably, the volume fraction α of the magnetic nanoparticles is $0.05<\alpha<0.15$. For in vitro applications, the toxicity of the magnetic nanoparticles must also be considered and this might impose a lower limit on the amount of magnetic nanoparticles that may be present in the microbubble shell.

There are several ways of mathematically expressing the constraints set out in (i) to (iv) of the method of the invention. A convenient way of expressing the constraint in (i) is represented by the inequality $|F_{BW}|>|W|$. It is preferred that the microbubble satisfies the inequality:

$$0 > \frac{F_{BW} + W}{W} > -1,$$

which expresses the requirement that the microbubble should remain suspended in the body of the carrier liquid (i.e. be marginally "sub-buoyant") to avoid the possibility that the microbubbles will burst by rising to the surface or by rapidly sinking to the bottom of the liquid. The weight (W) of the microbubble is defined herein as acting in the opposite direction to the force due to the buoyancy ($F_{BW}$) of the microbubble and, hence, is a negative quantity when $F_{BW}$ is positive.

Similarly, the requirement or constraint in (ii) above may be represented by the inequality $|F_M|>|F_{BW}+|W||$. More preferably, constraint (ii) is represented by the inequality $|F_M|>|F_{BW}+W|$, in order that the magnetic force is sufficient to overcome the force due to the buoyancy of the microbubble and its weight, irrespective of the direction of these forces.

The requirement in (iii) may be represented by the inequality $|F_M|>|F_D|$. The magnetic force ($F_M$) must be sufficient to overcome the force due to viscous drag ($F_D$), which may act in a different direction to the magnetic force ($F_M$) and will depend on the flow velocity of the carrier liquid. Thus, the signs of $F_D$ and $F_M$ may be different. $F_M$ is defined herein as a negative variable.

Requirement (iv) may be represented by the inequality:

$$\sigma_{scat} \geq \frac{4\pi\omega^4 \rho_l^2 R_{01}^6}{((k - m\omega^2)^2 + b^2\omega^2)};$$

where $$m = \rho_l R_{01}^2, b = 4\mu_l + \frac{3.6 \times 10^{-8}}{R_{01}}$$

and $$k = 3 \times 10^5 + \frac{0.24}{R_{01}}.$$

In the equation for $\sigma_{scat}$ above, ω is the frequency of the ultrasound, $\rho_l$ is the density of the carrier liquid (the liquid in which the microbubble is suspended), $R_{01}$ is the initial radius of the gas core of the microbubble and $\mu_l$ is the viscosity of the carrier liquid.

The scattering cross section of the microbubble is a function of the bubble's size, the nature of the surrounding liquid and the ultrasound excitation frequency. Typical values for the scattering cross section of microbubbles that are detectable and rupturable on exposure to ultrasound may be obtained by calculating $\sigma_{scat}$ for the commercially available SonoVue™ microbubbles.

The size of the shell relative to the gas core of the microbubble may be represented by the parameter ξ where:

$$\xi = \frac{R_2}{R_1} - 1,$$

$R_2$ is the radius of the microbubble and $R_1$ is the radius of the gas core. Generally, the radius of the gas core ($R_1$) of the microbubble is larger or equal to the thickness of the shell ($R_2-R_1$), and, preferably, $1 \geq \xi > 0$, more preferably, $0.5 \geq \xi > 0.1$.

There are a number of ways of mathematically determining the size of the shell relative to the gas core and the amount of nanoparticles in the shell of a microbubble that satisfies the conditions above. One way involves the use of the following parameters:

$$\psi = \frac{F_{BW} + W}{W}, \text{ where } 0 > \psi > -1; \quad (1)$$

$$\varphi = \frac{F_M}{F_{BW} + W}, \text{ where } \varphi < -1; \text{ and} \quad (2)$$

$$\lambda = \frac{F_M}{|F_D|}, \text{ where } \lambda < -1. \quad (3)$$

A line representing the limits for each of the parameters in (1) to (3) may be plotted on a single graph of the size of the shell relative to the gas core against the amount of nanoparticles in the shell, for a given magnetic field, ultrasound frequency and liquid flow velocity. A range of optimised microbubble designs may then be determined from the region on the graph that is defined by the intersection of the lines for the limits for each of the parameters ψ, φ and λ. Preferably, the value of φ and/or λ is each independently less than −2, more preferably −5.

The force due to buoyancy ($F_{BW}$) of the microbubble in the carrier liquid may be determined by the equation:

$$F_{BW} = \frac{4}{3}\pi g \rho_l R_2^3,$$

where g is the acceleration due to gravity, $\rho_l$ is the density of the carrier liquid.

The weight (W) of the microbubble may be determined by the equation:

$$W = -\frac{4}{3}\pi g[\rho_g R_1^3 + (R_2^3 - R_1^3)((1-\alpha)\rho_0 + \alpha\rho_{np})]$$

where $R_2$ is the radius of the microbubble, $\rho_g$ is the density of the gas in the gas core, $R_1$ is the radius of the gas core, α is the volume fraction of the magnetic nanoparticles in the shell of the microbubble, $\rho_0$ is the density of the liquid in which the nanoparticles are suspended, and $\rho_{np}$ is the density of the magnetic nanoparticles.

Generally, the shell of the magnetic microbubble has an outer coating or layer that is made of a different material to the liquid in which the magnetic nanoparticles are suspended. The outer coating surrounds or encapsulates an inner liquid layer of the shell in which magnetic nanoparticles are suspended. The thickness of the coating or external layer is negligible compared to the overall thickness of the shell and may be neglected from the equations that express of $F_M$, $F_D$, $F_{BW}$, W and $\sigma_{scat}$. It may also be convenient to neglect the volume of the outer coating when determining $\alpha$.

The magnetic force ($F_M$) on a microbubble from application of a magnetic field may be determined by the equation:

$$F_M = -\frac{4\pi\chi(B\cdot\nabla)B\alpha(R_2^3 - R_1^3)}{3\mu_0}$$

where $\chi$ is the effective volumetric susceptibility of the magnetic nanoparticles suspended in the shell, B is the strength of the applied magnetic field, $\alpha$ is the volume fraction of the magnetic nanoparticles in the shell of the microbubble, $R_2$ is the radius of the microbubble, $R_1$ is the radius of the gas core and $\mu_0$ is the permeability of free space.

The force due to viscous drag ($F_D$) on the microbubble, when the microbubble has been introduced into the liquid for cell transfection or delivery of a therapeutic agent (i.e. the carrier liquid) may be determined by:

$$F_D = \frac{u^2 C_D \pi R_{02}^6}{2},$$

where u is the flow velocity of the carrier liquid, $C_D$ is the drag coefficient (approximation for a solid sphere) and $R_{02}$ is the static radius of the microbubble. At equilibrium, the static outer radius $R_{02}$ will be the same as the time dependent outer radius $R_2$.

In many instances, the force due to viscous drag ($F_D$) on the microbubble in the carrier liquid may be determined by the equation for low velocity (laminar) flow:

$$F_D = 6\pi\mu_l u R_{02};$$

where $\mu_l$ is the viscosity of the carrier liquid, u is the flow velocity of the carrier liquid and $R_{02}$ is the static radius of the microbubble. Preferably, $F_D$ is expressed by the equation for low velocity (laminar flow).

The microbubble scattering cross section $\sigma_{scat}$ may be determined by the equation:

$$\sigma_{scat} = \frac{4\pi\omega^4 X^2 \rho_l^2 R_{01}^6}{p_{inc}^2}$$

where $\omega$ is the frequency of the ultrasound, X is the amplitude of the radial oscillation of the microbubble, $\rho_l$ is the density of the carrier liquid, $R_{01}$ is the initial radius of the gas core of the microbubble and $p_{inc}$ is the pressure amplitude of the ultrasound (provided by an external source).

The variables $F_M$, $F_D$, $F_{BW}$, W and $\sigma_{scat}$ may be better expressed using other equations, particularly in cases where the structure of the microbubble or the liquid in which it is to be used deviate from the ideal, classical situation as represented by the equations above. Other equations for determining $F_M$, $F_D$, $F_{BW}$, W and $\sigma_{scat}$ may be used in methods of the invention.

The field strength of the magnetic field to be applied should be known in order to determine whether a particular microbubble design satisfies the conditions above. In practice, the range of magnetic field strengths for actuating the microbubbles optimised microbubble formulations will be restricted by the field strengths of magnets that are currently available and are useable for the applications described herein. Thus, it is preferred that the requirements (ii) and (iii) above, are to be satisfied for an applied magnetic field B, where $120 \geq B \geq 0$ T, more preferably $15 \geq B \geq 0.01$ T, and even more preferred is $1.5 \geq B \geq 0.1$ T. The strength of the magnetic field will depend on the apparatus used. A magnetic field may be applied using a permanent magnet, a superconducting magnet or a pulsed (microsecond duration) magnet.

Similarly, there is, in practice, an upper limit for the flow velocity of the liquid in which the microbubbles will be used, before they will begin to burst. Preferably, the requirement of (iii) above is to be satisfied for a flow velocity, u, where $20 \geq u \geq 0$ ms$^{-1}$, more preferably $10 \geq u \geq 0.01$ ms$^{-1}$, and even more preferred is $5 \geq u \geq 0.1$ ms$^{-1}$. The upper limit for in vivo applications is typically 1.5 ms$^{-1}$. In some experiments, the flow velocity of the carrier liquid will be zero or nearly zero, such as in cell transfection experiments. Other experiments, including cell transfection experiments, may utilise higher flow velocities. However, in general, it may be necessary to measure the flow velocity of the carrier liquid in order to apply a method of the invention.

The identity of the liquid into which the suspension of microbubbles will be introduced will depend on the application. For example, in in vivo methods the microbubbles may be introduced into the bloodstream or lymph vessels of a human or animal body. For in vitro cell transfection experiments, the microbubbles may be added to the medium of a cell culture. Generally, an aqueous suspension of the microbubbles is used to introduce the microbubbles into the environment of their intended application. Preferably, the carrier liquid is water, a cell culture medium, human or animal blood, or human or animal lymph. Where the densities of these liquids are not available or have not been measured, then it may be necessary to estimate their values. Generally, the ultrasound frequency used to monitor and rupture the microbubbles will be known from the apparatus used to generate the ultrasound. However, the range of ultrasound frequencies available will also be limited, in practice, by the apparatus available to generate the ultrasound and to frequencies that are useable in the applications described herein. Thus, it is preferred that requirement (iv) is to be satisfied for an ultrasound frequency $\omega$, where $\omega = 2\pi f$ and $20 \geq f \geq 0.5$ MHz, preferably $15 \geq f \geq 1$ MHz.

In order to minimise the damping oscillations and inertial resistance of the microbubble shell, which will, in turn, maximise the amplitude of oscillation for a given bubble size and acoustic field, it is desirable that both the size of the shell relative to the gas core and the amount of magnetic nanoparticles in the shell of a microbubble are minimised. Preferably, a minimum size of the shell relative to that of the gas core is determined by methods of the invention. It is also preferred that a minimum amount of nanoparticles in the shell of a microbubble is determined, with or without minimisation of size of the shell relative to that of the gas core.

There may be a range of optimised microbubble formulations having different amounts of nanoparticles in the shell and sizes of the shell relative to the gas core that satisfy the constraints mentioned above for a given magnetic field, ultrasound frequency and flow velocity. It may therefore be necessary to select either an amount of nanoparticles in the shell or a size of the shell relative to the gas core, in order to determine the other parameter. The methods of the invention may include the step of selecting an amount of nanoparticles in the shell, or selecting a size of the shell relative to the gas core.

Once an amount of nanoparticles in the shell and a size of the shell relative to the gas core for a microbubble (i.e. an optimised microbubble) has been determined, then the amount of magnetic nanoparticles and the amount of liquid for the shell needed to prepare a suspension of the microbubbles is to be determined (step (b) in the method above). There is an empirical relationship between the amount of magnetic nanoparticles and solvent needed to prepare a suspension of optimised microbubbles and the amount of nanoparticles in the shell and the size of the shell relative to the gas core for the optimised microbubble design. For example, in some instances, the volume fraction of magnetic nanoparticles suspended or dissolved in a liquid used during preparation remains constant, such that the volume fraction of magnetic nanoparticles in the shell of the microbubbles is nearly the same as that initially used during preparation. Generally, an empirical relationship will need to be determined for the specific method used to prepare the suspension and the nature of the microbubble constituents.

A suspension of microbubbles may be prepared using standard methods known in the art, provided that the method takes into account the amount of magnetic nanoparticles and the amount of liquid for the shell needed to prepare a suspension of optimised microbubbles. A preferred way of preparing a suspension of the microbubbles comprises the step of shaking and/or sonicating an aqueous solution comprising a material for coating the microbubble shell, the magnetic nanoparticles and the liquid for the shell, then, typically, allowing the solution to settle before extracting a lower part of the solution.

The suspension may be prepared by forming, in an aqueous solution, an emulsion of the ingredients for forming the microbubble, followed by shaking and/or sonicating. The sonication and/or shaking step is typically carried out under an atmosphere of the gas that is to be trapped as the gas core of the microbubbles. Sonication or shaking may be performed until formation of a foam.

The gas for the gas core of the microbubble suspension may be bubbled through the aqueous solution used to prepare the suspension in addition to, or as an alternative to, carrying out sonication and/or shaking under an atmosphere of the desired gas. Suitable gases for the gas core are described below.

Generally, a material for coating the microbubble shell is added to the aqueous solution, such as phosphate buffered saline (PBS), used to prepare the suspension of microbubbles. The coating material forms the outer layer of the microbubble shell, such that the magnetic nanoparticles are suspended in a liquid layer around the gas core. The coating material may form an additional inner layer in the shell, which separates the core and the solvent layer. Examples of suitable coating materials are described below. The suspension or solution of the nanoparticles may be added to the aqueous solution for preparing the microbubbles before or after the coating material is added. Examples of suitable magnetic nanoparticles are described below.

In order to form microbubbles, the shell liquid and shell coating material are selected to form a stable emulsion in an aqueous solution. Generally, the liquid used to form the liquid layer of the microbubble shell is a hydrophobic solvent. The liquid is selected for its chemical compatibility with the magnetic nanoparticles and examples of suitable liquids are described below.

A suspension of microbubbles, which may have been prepared according to the sonication/shaking method outlined above, or according to a method known in the art, may be filtered to obtain a suspension having a desired distribution of optimised microbubbles.

In embodiments where an agent, preferably a therapeutic agent (including genetic material for cell transfection), is incorporated in the microbubble for delivery to a target site, then the therapeutic agent may be suspended or dissolved in a liquid layer of the shell. This may be the same layer in which the magnetic nanoparticles are suspended or an alternative layer. It may be necessary to modify the therapeutic agent for suspension or dissolution in a layer of the shell, but this may be achieved using methods known in the art. Alternatively, the therapeutic agent may be attached to, or incorporated in, the external coating of the microbubble using methods known in the art.

A further aspect of the invention relates to a computer program comprising computer-executable code that when executed on a computer system causes the computer to perform a method of the invention. An embodiment of the invention relates to a computer program comprising computer-executable code that when executed on a computer system cause the computer to perform a method for use in the preparation of a suspension of microbubbles for use in a carrier liquid, wherein the microbubbles have a gas core and a liquid shell, said liquid shell comprising magnetic nanoparticles, and wherein the method comprises the step of:

(a) receiving values of the magnetic field B and the ultrasound frequency ω to be applied to the microbubble, and the flow velocity u of the carrier liquid;

(b) using the values of B, ω and u to determine a size of the shell relative to the gas core and an amount of nanoparticles in the shell of a microbubble by applying the following conditions:
  (i) the force due to buoyancy ($F_{BW}$) of the microbubble in the carrier liquid is greater than the weight (W) of the microbubble;
  (ii) the magnetic force ($F_M$) on the microbubble due to said magnetic field applied to the carrier liquid is greater than the combined weight (W) and force due to buoyancy ($F_{BW}$) of the microbubble;
  (iii) said magnetic force ($F_M$) on the microbubble is greater than the force due to viscous drag ($F_D$) on the microbubble due to flow of the carrier liquid; and
  (iv) the scattering cross section ($\sigma_{scat}$) of the microbubble to ultrasound allows the microbubble to be detectable and rupturable on exposure to ultrasound;

(c) using the amount of nanoparticles in the shell and the relative size of the shell to the gas core of the microbubble to determine the amount of magnetic nanoparticles and the amount of liquid for the shell needed to prepare a suspension of the microbubbles; and (d) outputting the amount of magnetic nanoparticles and the amount of liquid for the shell needed to prepare the suspension.

A user may need to input the values of B, ω and/or u into the computer system. Other constants, such as the densities of the materials from which the microbubble is composed and the density of the carrier liquid of use, may need to be input into the data-processing means by the user. Where the components of the microbubble are the same and the microbubbles are for use in an application where the same applied magnetic field B and ultrasound frequency ω are used repeatedly, then the computer program may comprise computer-executable code to prompt the user to confirm that B and ω are the same as that used previously.

For some applications, such as for intravenous injection of the microbubbles into a human or animal body, it may be necessary to measure the flow velocity of the liquid into which the microbubbles are to be introduced. For example, the flow velocity of a patient's blood may be determined from their blood pressure, which is then input into the computer system. The computer system may have, or be connected to, a measurement means for determining the flow velocity of the liquid, such as a device for measuring the blood pressure of a patient.

For other applications, such as in vitro cell transfection, the same type of cell medium may be used repeatedly and the computer program may then comprise computer-executable code to prompt the user to confirm that u is the same as that used previously.

The computer program may comprise computer-executable code that prompts the user to select the variables from a list. For example, the program may contain data for the densities of some commonly used liquids.

Similarly, the computer system may have, or be connected to, magnetic field generating apparatus, which generates the magnetic field to be applied to the microbubbles, and/or ultrasound generating apparatus, which generates the ultrasound to be applied to the microbubbles. The computer system may then simply receive the value of B that has been set on the magnetic field generating apparatus and/or the value of ω that has been set on the ultrasound generating apparatus to perform a method of the invention.

Where there are a range of microbubble designs that satisfy conditions (i) to (iv), and optionally any further conditions mentioned in relation to the methods of the invention, then the computer program may comprise computer-executable code to prompt the user to input one of an amount of magnetic nanoparticles in the shell or a size of the shell relative to the gas core.

Where the computer program is to perform a method of preparing a suspension of microbubbles, then the computer system may be connected to an apparatus for automatically preparing a suspension of magnetic nanoparticles. Such apparatus are well known in the art, particularly in the field of combinatorial chemistry. The amount of magnetic nanoparticles and the amount of liquid for the shell needed to prepare the suspension, as determined by running the computer program to perform a method of the invention, is then output to the preparative means. The preparative means may then automatically prepare a suspension of optimised microbubbles, such as by using the sonicating/shaking method described above.

The invention also relates to a computer-readable medium storing a computer program of the invention and a computer program product comprising a signal comprising a computer program of the invention.

Another aspect of the invention relates to a suspension of microbubbles obtained or obtainable by the preparative methods of the invention.

The invention also relates to a suspension of microbubbles for use in a carrier liquid; wherein the microbubbles have a gas core and a liquid shell, said liquid shell comprising magnetic nanoparticles, and wherein substantially all of the microbubbles satisfy the following conditions:

(i) the force due to buoyancy ($F_{BW}$) of the microbubble in the carrier liquid is greater than the weight (W) of the microbubble;

(ii) the magnetic force ($F_M$) on the microbubble due to a magnetic field applied to the carrier liquid is greater than the combined weight (W) and force due to buoyancy ($F_{BW}$) of the microbubble;

(iii) said magnetic force ($F_M$) on the microbubble is greater than the force due to viscous drag ($F_D$) on the microbubble due to flow of the carrier liquid; and (iv) the scattering cross section ($\sigma_{scat}$) of the microbubble to ultrasound allows the microbubble to be detectable and rupturable on exposure to ultrasound.

The term "substantially all" refers to a suspension where 80%, preferably 90%, more preferably 95% and even more preferred 99% of the microbubbles in the suspension fulfil all of the constraints set out above.

The microbubbles of the invention have a gas core. Generally, the gas for the gas core has a reflectivity that is suitable for the microbubble to be effective as an ultrasound contrast agent. The gas is also selected for the application in which the microbubbles are to be used. Typically, the gas is inert and biocompatible. For example, for in vivo applications, the gas should not be toxic (in the amounts used) to the human or animal body. For cell transfection applications, the gas should not be cytotoxic. Suitable gases include, for example, air, nitrogen, carbon dioxide, oxygen, noble gases (e.g. helium, neon, argon, xenon), perfluorocarbon gases (e.g. perfluoropropane) and mixtures thereof. Preferably, the gas core of the microbubble is selected from air, a noble gas, carbon dioxide, nitrogen, oxygen and mixtures thereof. More preferably the gas core is air.

The magnetic nanoparticles may be composed of a variety of magnetic metals, such as iron, cobalt or nickel. Preferably, the magnetic nanoparticles are ferromagnetic nanoparticles, such as iron oxide nanoparticles. The nanoparticles may contain various metal elements, such as Zn, Co and Ni, to control their magnetic characteristics. The iron oxide nanoparticles may comprise, as a main component, magnetite ($Fe_3O_4$), maghemite ($\gamma$-$Fe_2O_3$), $Fe_3O_4$ and mixed ferrite. The average particle size of the magnetic nanoparticles is usually from 5 to 30 nm, preferably from 6 to 25 nm, more preferably from 8 to 12 nm.

In order to aid suspension or dissolution of the magnetic nanoparticles in the shell, the magnetic nanoparticles may be coated. The coating is selected to aid dispersibility or solubility of the magnetic nanoparticles and the coating used will depend on the liquid used to form part or all of the shell. Preferably, the magnetic nanoparticles are coated with a surfactant.

The microbubbles comprise magnetic nanoparticles suspended in a liquid layer of the shell and an external coating. The liquid layer should be chemically compatible with the coating material and should be suitable for the application in which the microbubbles are to be used (e.g. a non-toxic liquid should be used for in vivo applications). The liquid shell of the microbubble preferably comprises a hydrocarbon oil, preferably a non-volatile hydrocarbon oil, or derivatives thereof in a liquid layer. Suitable hydrocarbon oils include non-polar hydrocarbon oils (e.g. mineral oils) and hydrocarbon oils of plant or animal origin. Examples of non-polar hydrocarbon oils include isoparaffin, squalene, perhydrosqualene, paraffin oils, petroleum oils, hydrogenated or partially hydrogenated polyisobutene, isoeicosane, decene/butene copolymers, polybutene/polyisobutene copolymers and mixtures thereof. Examples of hydrocarbon oils of plant origin include wheatgerm oil, sunflower oil, grapeseed oil, groundnut oil, sesame seed oil, maize oil, apricot kernel oil, castor oil, shea oil, avocado oil, coconut oil, corn oil, olive oil, soybean oil, sweet almond oil, palm oil, rapeseed oil, cotton seed oil, hazelnut oil, macadamia oil, jojoba oil, alfalfa oil, poppy oil, evening primrose oil and mixtures thereof. It is preferred that the liquid shell comprises isoparaffin or soybean oil, more preferably a liquid layer of the shell is isoparaffin.

The shell may also comprise an external coating that is a polymer, a surfactant or a lipid. Typically, the coating is an amphiphilic molecule, such as a medium or long chain aliphatic acid residue, a medium or long chain alkyl group and a hydrophilic group, or a polymer. Examples of suitable amphiphilic molecules are lipid or surfactants. Suitable lipids include phospholipids and/or glycolipids. Examples of lipids include phosphatidylcholine, phosphatidylethanolamine, phosphatidylserine, phosphatidylglycerol, phosphatidic acid, phosphatidylinositol, dipalmitoylphosphatidylcholine (DPPC), distearoylphosphatidylcholine (DSPC), dimyristoyiphosphatidylcholine (DMPC), dioleylphosphatidylcholine (DOPE), dimyristoylphosphatidylethanolamine, dipalmitolphosphatidylethanolamine, distearoylphosphatidylethanolamine, lysolipids, fatty acids, cardiolipin, sphingomyelin, glycosphingolipids, glucolipids, glycolipids, sulphatides, lipids with ether and ester-linked fatty acids, polymerizable lipids, and combinations thereof. The lipids used may be of either natural or synthetic origin. There are also usable phospholipids derived from plants and animals such as egg yolk or soybeans and their hydrogenation products or hydroxide derivatives, so-called semi-synthetic phospholipids. Fatty acids constituting a phospholipid are not specifically limited, and saturated and unsaturated fatty acids are usable. Preferably, the material is hydrogenated L-α-phosphatidylcholine.

In some instances, the surface of the microbubble may be modified with a polymer, such as, for example, with polyethylene glycol (PEG), using procedures readily apparent to those skilled in the art. Surface modification of the microbubble is one way of attaching agents, such as therapeutic agents, to a microbubble. In one embodiment of the invention, a therapeutic agent is attached to the coating of the microbubble.

In another embodiment, a therapeutic agent may be suspended or dissolved in a liquid layer of the microbubble shell. The therapeutic agent should be chemically compatible with the liquid layer. It may be necessary to modify the therapeutic agent to aid its suspendability or solubility in the liquid layer using standard methods known in the art.

A further embodiment relates to a suspension comprising a therapeutic agent i.e. the therapeutic agent is not attached to or part of a microbubble.

The amount of therapeutic agent included in the suspension or as part of the microbubble will depend on the specific application. The therapeutic agent may include, for example, prodrugs, pharmaceutical agents, drugs, synthetic organic molecules, proteins, peptides, vitamins, steroids, steroid analogs and genetic material, including nucleosides, nucleotides and polynucleotides, including deoxyribonucleic acid (DNA) and ribonucleic acid (RNA). The genetic material may be made by synthetic chemical methodology known to one of ordinary skill in the art, or by the use of recombinant technology, or by a combination thereof. The DNA and RNA may optionally comprise unnatural nucleotides and may be single or double stranded.

For in vivo applications, it is preferred that the therapeutic agent is attached to or encapsulated within the microbubble. Therapeutic agents may be selected from:

anti-allergic agents (e.g. amelexanox);
anti-anginals (e.g. diltiazem, nifedipine, verapamil, erythrityl tetranitrate, isosorbide dinitrate, nitroglycerin (glyceryl trinitrate) and pentaerythritol tetranitrate);
anticoagulants (e.g. phenprocoumon, heparin);
antibodies, (e.g. a polyclonal antibody or a monoclonal antibody. Examples include CD44, CD54, CD56, Fas);
antibiotics (e.g. dapsone, chloramphenicol, neomycin, cefaclor, cefadroxil, cephalexin, cephradine erythromycin, clindamycin, lincomycin, amoxicillin, ampicillin, bacampicillin, carbenicillin, dicloxacillin, cyclacillin, picloxacillin, hetacillin, methicillin, nafcillin, oxacillin, penicillin G, penicillin V, ticarcillin, rifampin and tetracycline);
anti-cancer agents (e.g. platinum compounds, such as spiroplatin, cisplatin and carboplatin) methotrexate, adriamycin, taxol, mitomycin, ansamitocin, bleomycin, cytosine arabinoside, arabinosyl adenine, mercaptopolylysine, vincristine, busulfan, chlorambucil, melphalan (e.g., L-sarolysin (L-PAM, also known as Alkeran) and phenylalanine mustard (PAM)), mercaptopurine, mitotane, procarbazine hydrochloride, dactinomycin (actinomycin D), daunorubicin hydrochloride, doxorubicin hydrochloride, mitomycin, plicamycin (mithramycin), paclitaxel aminoglutethimide, estramustine phosphate sodium, flutamide, leuprolide acetate, megestrol acetate, tamoxifen citrate, testolactone, trilostane, amsacrine (m-AMSA), asparaginase (L-asparaginase) Erwina asparaginase, etoposide (VP-16), interferon a-2a, interferon a-2b, teniposide (VM-26), vinblastine sulfate (VLB), vincristine sulfate, bleomycin, bleomycin sulfate, methotrexate, adriamycin, carzelesin, arabinosyl, aziridinylbenzoquinone, muramyl-tripeptide and 5-fluorouracil), anti-coagulation agents (e.g. phenprocoumon and heparin);
anti-fungal agents, (e.g. ketoconazole, nystatin, griseofulvin, flucytosine (5-fc), miconazole, amphotericin B, ricin, and P-lactam antibiotics, such as sulfazecin);
anti-inflammatories;
anti-parasitics;
anti-protozoans (e.g. chloroquine, hydroxychloroquine, metronidazole, quinine and meglumine antimonate);
anti-rheumatics (e.g. penicillamine);
antituberculars (e.g. para-aminosalicylic acid, isoniazid, capreomycin sulfate cycloserine, ethambutol hydrochloride ethionamide, pyrazinamide, rifampin, and streptomycin sulfate);
anti-virals (e.g. acyclovir, amantadine azidothymidine, such as AZT or Zidovudine, ribavirin, amantadine, vidarabine and vidarabine monohydrate);
antiinflammatories (e.g. difunisal, ibuprofen, indomethacin, meclofenamate, mefenamic acid, naproxen, oxyphenbutazone, phenylbutazone, piroxicam, sulindac, tolmetin, aspirin and salicylates);
biological response modifiers (e.g. muramyldipeptide, muramyltripeptide, prostaglandins, microbial cell wall components, lymphokines, such as bacterial endotoxin (lipopoly-saccharide, macrophage activation factor), sub-units of bacteria, such as Mycobacteria and Corynebacteria, the synthetic dipeptide N-acetyl-muramyl-L-alanyl-D-isoglutamine); vitamins (e.g. cyanocobalamin neinoic acid, retinoids and derivatives such as retinol palmitate, a-tocopherol, naphthoquinone, cholecalciferol, folic acid, and tetrahydrofolate);

blood products (e.g. parenteral iron, hemin, hematoporphyrins and their derivatives);

cardiac glycosides (e.g. deslanoside, digitoxin, digoxin, digitalin and digitalis);

circulatory drugs (e.g. propranolol);

hormones or steroids (e.g. growth hormone, melanocyte stimulating hormone, estradiol, beclomethasone dipropionate, betamethasone, betamethasone acetate and betamethasone sodium phosphate, vetamethasone disodium phosphate, vetamethasone sodium phosphate, cortisone acetate, dexamethasone, dexamethasone acetate, dexamethasone sodium phosphate, flunsolide, hydrocortisone, hydrocortisone acetate, hydrocortisone cypionate, hydrocortisone sodium phosphate, hydrocortisone sodium succinate, methylprednisolone, methylprednisolone acetate, methylprednisolone sodium succinate, paramethasone acetate, prednisolone, prednisolone acetate, prednisolone sodium phosphate, prednisolone tebutate, prednisone, triamcinolone, triamcinolone acetonide, triamcinolone diacetate, triamcinolone hexacetonide, fludrocortisone acetate, progesterone, testosterone, and adrenocorticotropic hormone);

narcotics (e.g. paregoric and opiates, such as codeine, heroin, methadone, morphine and opium);

metal poisoning antidotes;

neuromuscular blockers (e.g. atracurium besylate, gallamine triethiodide, hexafluorenium bromide, metocurine iodide, pancuronium bromide, succinylcholine chloride, tubocurarine chloride and vecuronium bromide);

peptides (e.g. angiostatin, manganese super oxide dismutase, tissue plasminogen activator, glutathione, insulin, dopamine, human chorionic gonadotropin, corticotropin release factor, cholecystokinins, bradykinins, promoters of bradykinins, inhibitors of bradykinins, elastins, vasopressins, pepsins, glucagon, integrins, Angiotensin Converting Enzyme (ACE) inhibitors (captopril, enalapril, and lisinopril), adrenocorticotropic hormone, oxytocin, calcitonins, IgG, IgA, IgM, ligands for Effector Cell Protease Receptors, thrombin, streptokinase, urokinase, Protein Kinase C, interferon, colony stimulating factors, granulocyte colony stimulating factors, granulocyte-macrophage colony stimulating factors, tumor necrosis factors, nerve growth factors, platelet derived growth factors, lymphotoxin, epidermal growth factors, fibroblast growth factors, vascular endothelial cell growth factors, erythropoietin, transforming growth factors, oncostatin M, interleukins (interleukin 1, interleukin 2, interleukin 3, interleukin 4, interleukin 5, interleukin 6, interleukin 7, interleukin 8, interleukin 9, interleukin 10, interleukin 11, and interleukin 12), metalloprotein kinase ligands, and collagenases);

enzymes (e.g. alkaline phosphatase and cyclooxygenases);

metabolic potentiators (e.g. glutathione); and sedatives (e.g. amobarbital, amobarbital sodium, aprobarbital, butabarbital sodium, chloral hydrate, ethchlorvynol, ethinamate, flurazepam hydrochloride, glutethimide, methotrimeprazine hydrochloride, methyprylon, midazolam hydrochloride, paraldehyde, pentobarbital, pentobarbital sodium, phenobarbital sodium, secobarbital sodium, talbutal, temazepam and triazolam).

The suspension will contain a distribution of microbubbles having different microbubble structures. It is preferred that the distribution is centred on the optimised microbubble structure determined by a method of the invention. For use in the applications described herein, it is preferred that the microbubbles have a diameter from 1 µm to 10 µm, preferably 1 to 5 µm. The relative thickness of the shell to the overall diameter of the microbubble should satisfy the conditions for optimising the microbubble structure set out above. The standard deviation of microbubble diameters in a distribution representing a suspension of the microbubbles is preferably ±3 µm, more preferably ±1 µm.

For intravenous administration, it is preferred that the diameter of the microbubbles is less than or equal to 8 µm. There is a risk that microbubbles above a certain size could cause an embolism to form in the body.

Another aspect of the invention relates to a suspension of microbubbles according to the invention for use in the treatment of the human or animal body. The invention also relates to methods of medical treatment involving the use of the suspension of the invention, and also the use of a suspension of the invention in the manufacture of a medicament for use in the treatment of the human or animal body. Suspensions or magnetic microbubbles for the treatment of the human or animal body comprise a therapeutic agent, which is preferably attached to or incorporated in the microbubbles. The method of medical treatment of a human or animal body comprises the steps of:

(a) administering a suspension of microbubbles of the invention, or medicament in the use of the invention, to the human or animal body;

(b) optionally monitoring the position of the microbubbles using ultrasound;

(c) actuating the microbubbles in vivo using an applied magnetic field to a target site of therapeutic interest; and (d) rupturing the microbubbles using ultrasound at the target site.

A suspension of microbubbles is generally introduced intravenously or into lymph vessels at or near the area to be treated. Preferably, the suspension of microbubbles is introduced intravenously. The area is then exposed to ultrasound to image the area and to determine the location of the microbubbles. A magnetic field is then applied to move the microbubbles to the desired location and to keep them there. Once the microbubbles are at the intended target, they are exposed to ultrasound at a frequency and an intensity that is sufficient to rupture the bubbles. The optional step of monitoring the microbubbles using ultrasound is generally performed with ultrasound of a lower intensity than that used to rupture the microbubbles.

The quantity of microbubbles that may be administered to a patient will depend on the specific microbubble formulation used and the therapeutic agent that is to be delivered. It is, in general, preferred that a dose of the microbubble formulation should not exceed 1 cc/kg, preferably 0.3 cc/kg, and more preferably 0.15 cc/kg.

The delivery of therapeutic agents in accordance with the invention using ultrasound is best accomplished for tissues that have a good acoustic window for the transmission of ultrasonic energy. This is the case for most tissues in the body, such as muscle, the heart, the liver and most other vital structures. In order to treat a site in the brain, it may be necessary to create a surgical window in the skull in order to be able to direct ultrasound to the target site.

Another aspect of the invention is an in vitro method of cell transfection, wherein the method comprises:

(a) providing a container for a cell culture, wherein the container comprises a medium and cells on a surface of the container;

(b) adding to the medium a suspension of microbubbles;

(c) actuating the microbubbles to the surface of the container using an applied magnetic field; and (d) rupturing the microbubbles at the surface using ultrasound.

The microbubbles, or the suspension of microbubbles, comprise genetic material for transfection, preferably DNA or RNA for transfection. The sonoporation effect allows advantageous uptake of the genetic material for cell transfection. Containers for cell culture and media for culturing cells for use in the method are well known in the art.

The method is performed using a magnetic field of strength $120 \geq B \geq 0$ T, preferably $15 \geq B \geq 0.01$ T and even more preferred is $1.5 \geq B \geq 0.1$ T. The ultrasound frequency ω applied to rupture the microbubbles is preferably $20 \geq f \geq 0.5$ MHz, more preferably $15 \geq f \geq 1$ MHz, where $\omega = 2\pi f$. Typically, peak negative pressures of from 0.5 to 1 MPa are generally suitable for rupturing microbubbles of the invention.

A further aspect of the invention relates to an in vitro cell culture assay method, which comprises the steps of:
(a) providing a container for a cell culture, wherein the container comprises a medium and cells of a cell line on a surface of the container;
(b) adding to the medium a suspension of microbubbles;
(c) actuating the microbubbles to the surface using an applied magnetic field; and
(d) rupturing the microbubbles at the surface using ultrasound;
(e) determining the cytotoxicity of the agent to the cells of the cell line.

The microbubbles, or the suspension of microbubbles, comprise an agent, such as a potential new drug, that is to be assayed for its therapeutic activity. The method overcomes problems associated with delivery of therapeutic agents through the membrane of a cell because of the sonoporation effect. The method may be performed using the magnetic field strength and/or ultrasound frequency set out above for the in vitro cell transfection method.

In principle, any cell line known in the art may be used with the assay method. For example, suitable cell lines include A172 (glioma), A549 (lung cancer), BCP-1 cells (PEL), HEK 293 cells (kidney), HeLa (cervical cancer), HL60 (promyelocytic leukemia), K562 (chronic myeloid leukemia), KG-1 (myelogenous leukaemia), Jurkat cell line, Lncap (Prostate Cancer), MCF-7 (breast cancer), MDA-MB-438 (breast cancer), T47D (breast cancer), THP-1 (acute myeloid leukemia), U87 (glioblastoma), SHSY5Y Human neuroblastoma cells and cell lines available from the National Cancer Institute. Animal cell lines, such as the primate cell lines: Vero (African green monkey Chlorocebus kidney epithelial cell line), COS-7 (African Green Monkey Kidney Cells); rat tumour cell lines: GH3 (pituitary tumor), 9L (glioblastoma), PC12 (pheochromocytoma); and mouse cell lines: 3T3 (embryonic fibroblast), MC3T3 (embryonic calvarial), C3H-10T1/2 (embryonic mesenchymal); are not excluded.

The step of determining the cytotoxicity of the agent to the cells of the cell line will depend on the agent that has been tested and the cell line that has been used. This step is performed using methods known in the art.

The steps in the method of medical treatment, the in vitro method of cell transfection and/or the in vitro cell culture assay method may be performed after the method of preparing a suspension of microbubbles of the invention, or after the method of determining a size of the shell relative to the gas core and an amount of nanoparticles in the shell for a microbubble of the invention.

$R_1$ represents the radius of the gas core of the microbubble and $R_2$ is the radius of the microbubble.

Figure 2:
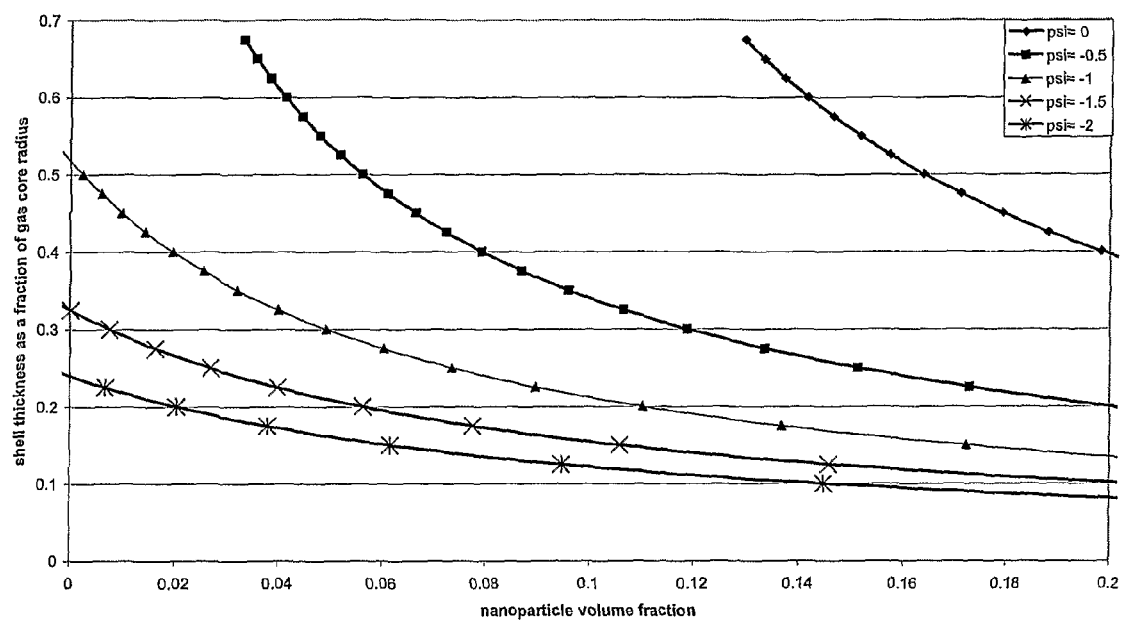

FIG. 2 is graph axis showing different values of ψ (ψ is 0, −0.5, −1, −1.5 or −2), where nanoparticle volume fraction is plotted on the x-axis and shell thickness as a fraction of gas core radius is plotted on the y-axis.

Figure 3:
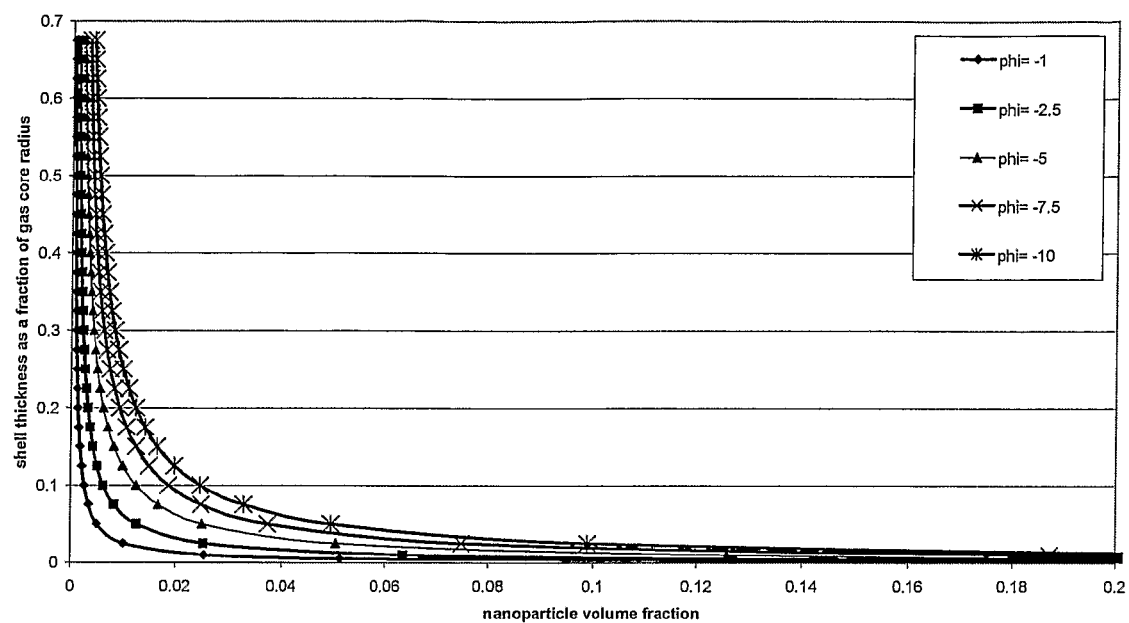

FIG. 3 is graph axis showing different values of φ (φ is −1, −2.5, −6, −7.5 or −10) for a given magnetic field ((B·∇)B=18 $T^2$/m has been used as an example), where nanoparticle volume fraction is plotted on the x-axis and shell thickness as a fraction of gas core radius is plotted on the y-axis.

Figure 4:
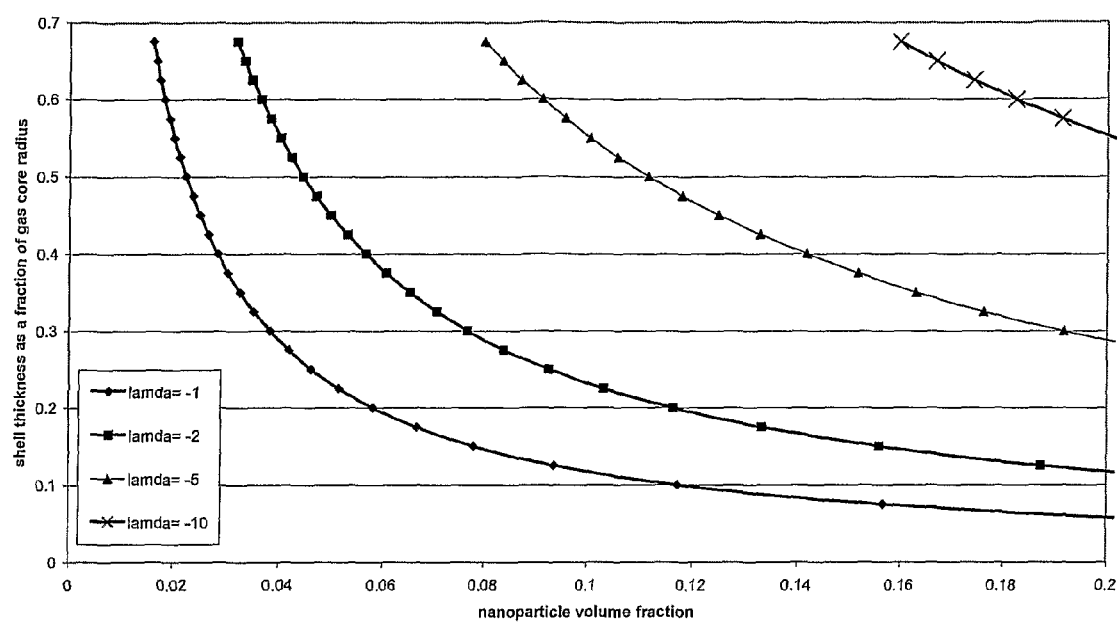

FIG. 4 is graph axis showing different values of λ (λ is −1, −2, −5 or −10) for a given magnetic field and flow velocity (B·∇)B=18 $T^2$/m and a flow velocity of $10^{-4}$ m/s have been used as an example), where nanoparticle volume fraction is plotted on the x-axis and shell thickness as a fraction of gas core radius is plotted on the y-axis.

Figure 5:
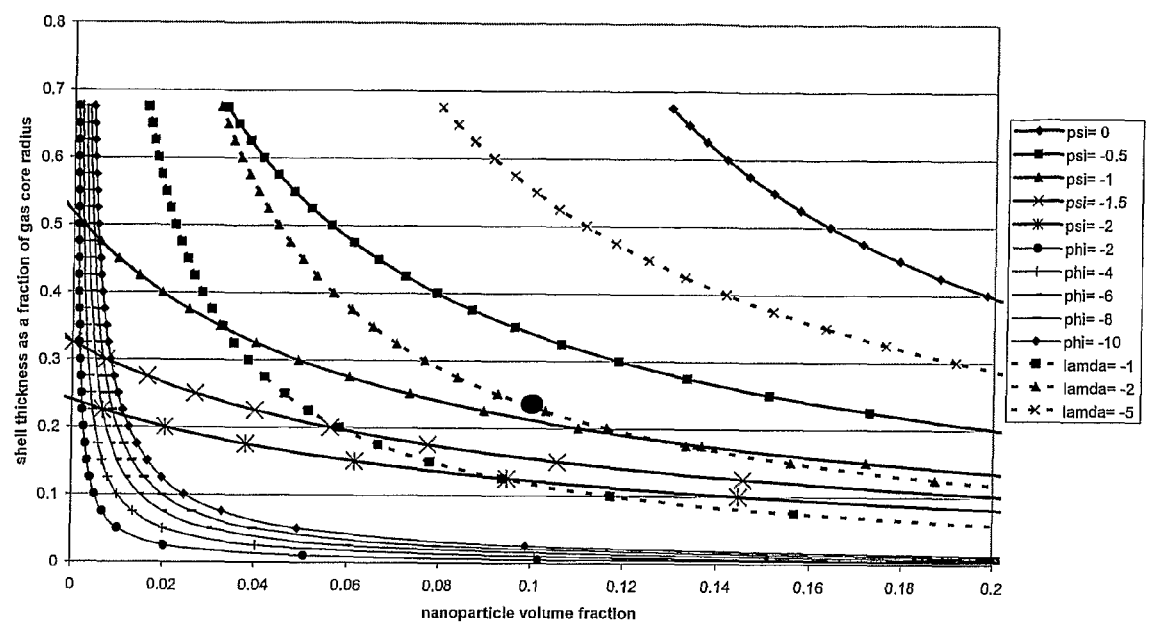

FIG. 5 is a formulation map obtained by combining graphs for ψ, φ and λ, such as FIGS. 2 to 4, and it shows the range of microbubble designs that satisfy the conditions set out for ψ, φ and λ for (B·∇)B=18 $T^2$/m and a flow velocity of $10^{-4}$ m/s. An optimised microbubble design is represented by a circle in the figure.

FIG. 6 are drawings showing the separation that occurs in various microbubble preparations after standing for 15 and 30 minutes.

FIG. 7 are drawings showing the magnetic response of different microbubble preparations after being placed near a magnet. Label (i) is a photograph of preparation C(i) 10 s after it was placed near a magnet. Label (ii) is a photograph of preparation C(i) 1 min after it was placed near a magnet. Label (iii) is a photograph of preparation A 10 s after it was placed near a magnet. Label (iv) is a photograph of preparation B 10 s after it was placed near a magnet.

Figure 8:
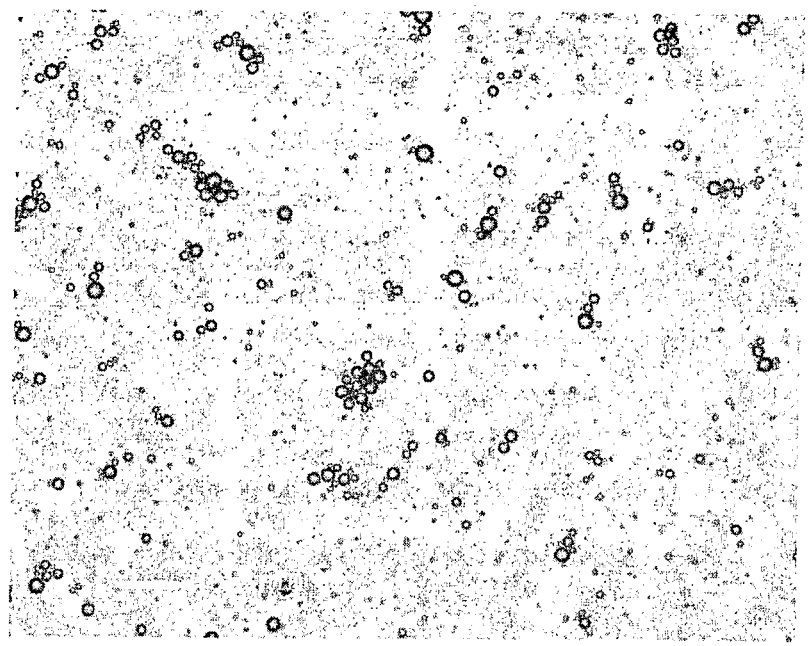

FIG. 8 is a photograph taken through a microscope of preparation C(i), which is focused on the buoyant material (the underlying grid of the haemocytometer slide is also shown out-of-focus).

Figure 9:
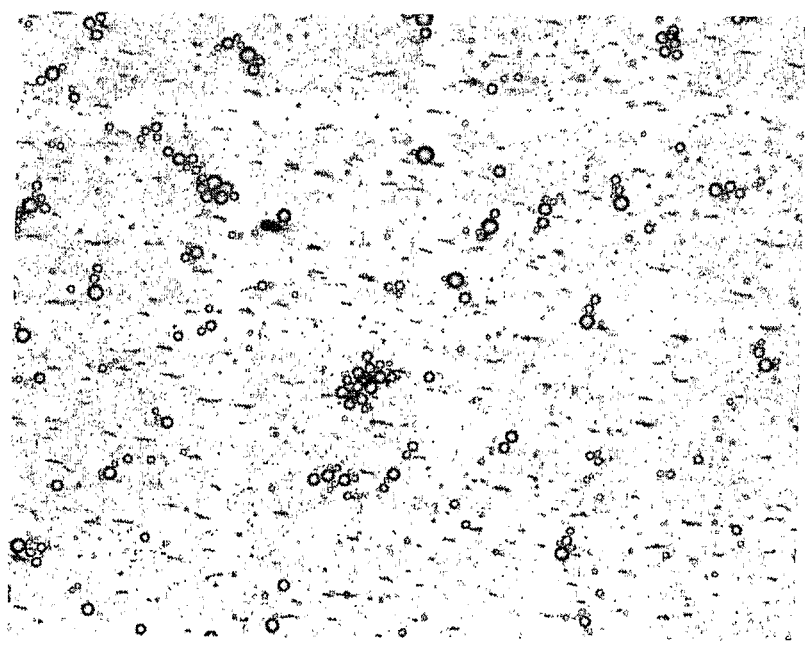

FIG. 9 is a photograph taken through a microscope of preparation C(i) after a single bar magnet was held to the side and slightly above the level of the microscope slide.

Figure 10:
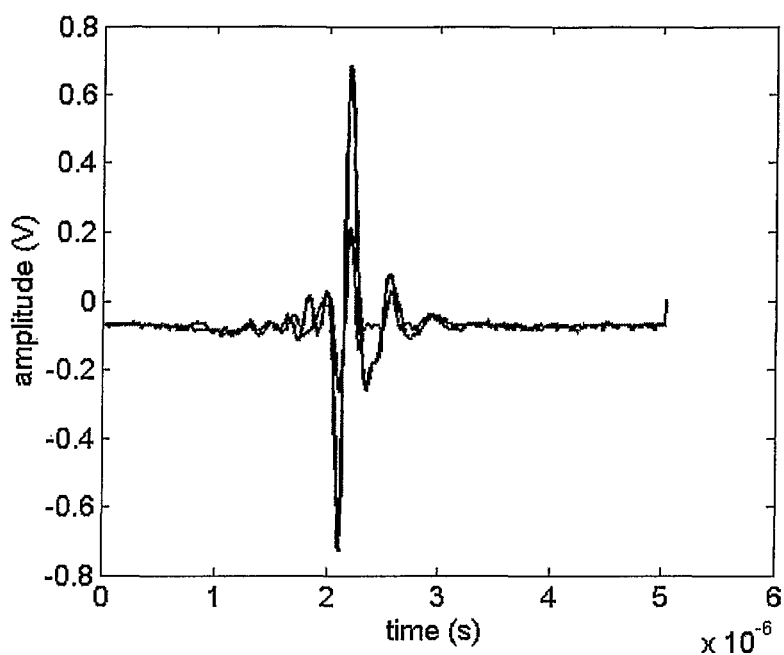

FIG. 10 is a graph showing the attenuation of an ultrasound pulse in the suspension of magnetic microbubbles. The darker line in the graph represents the microbubbles of preparation C(i) and the lighter line represents water.

Figure 11:
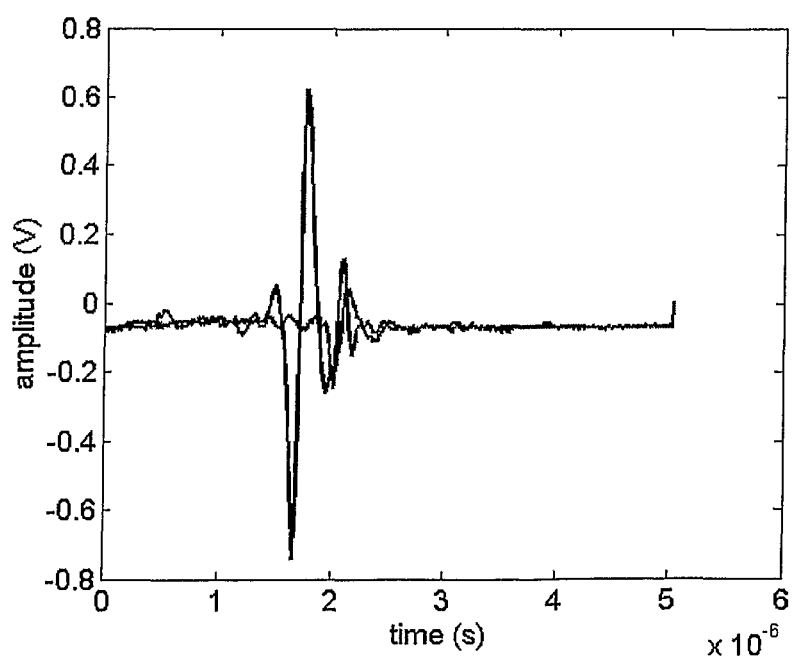

FIG. 11 is a graph showing the attenuation of an ultrasound pulse in the suspension of SonoVue™ microbubbles. The darker line in the graph represents the SonoVue™ microbubbles and the lighter line represents water.

Figure 12:
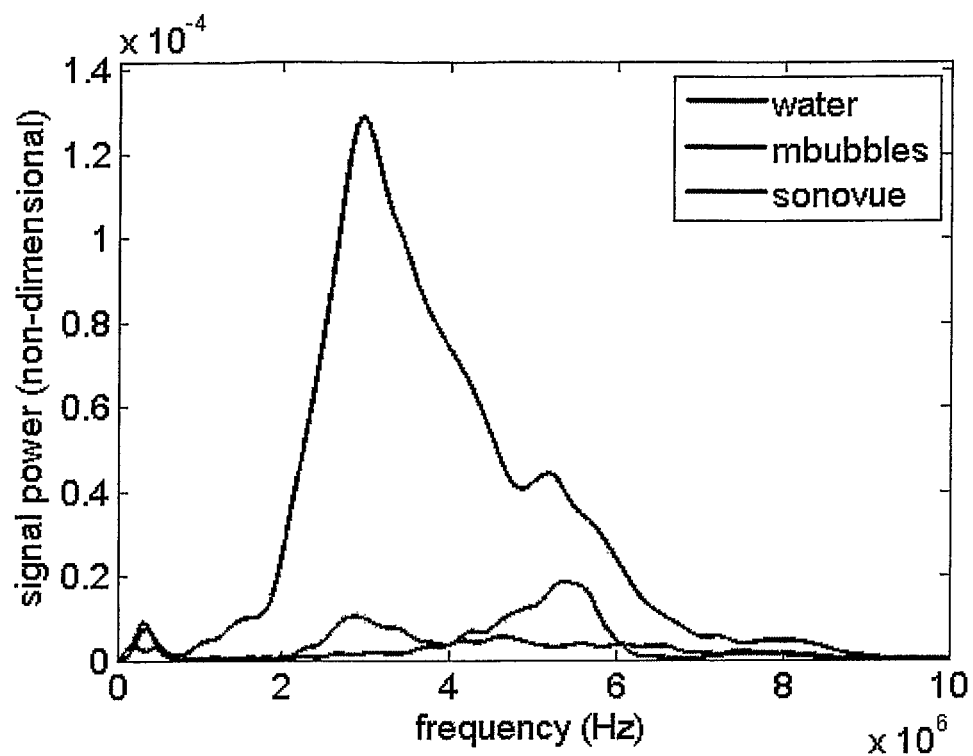

FIG. 12 is a graph showing frequency spectra for an ultrasound pulse propagated through a suspension of magnetic microbubbles, a suspension of SonoVue™ microbubbles and water.

Figure 13:
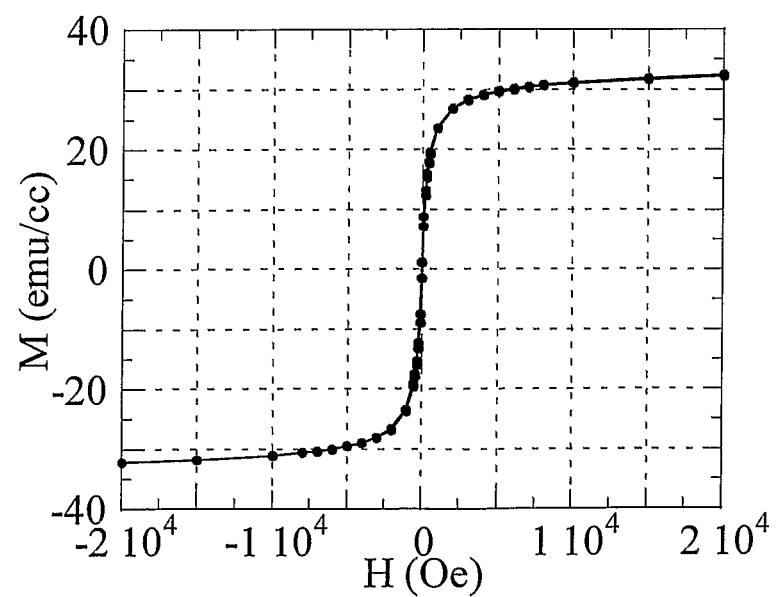

FIG. 13 is a graph showing a magnetisation curve of the magnetic nanoparticle suspension that was used to prepare the microbubbles.

Figure 14:
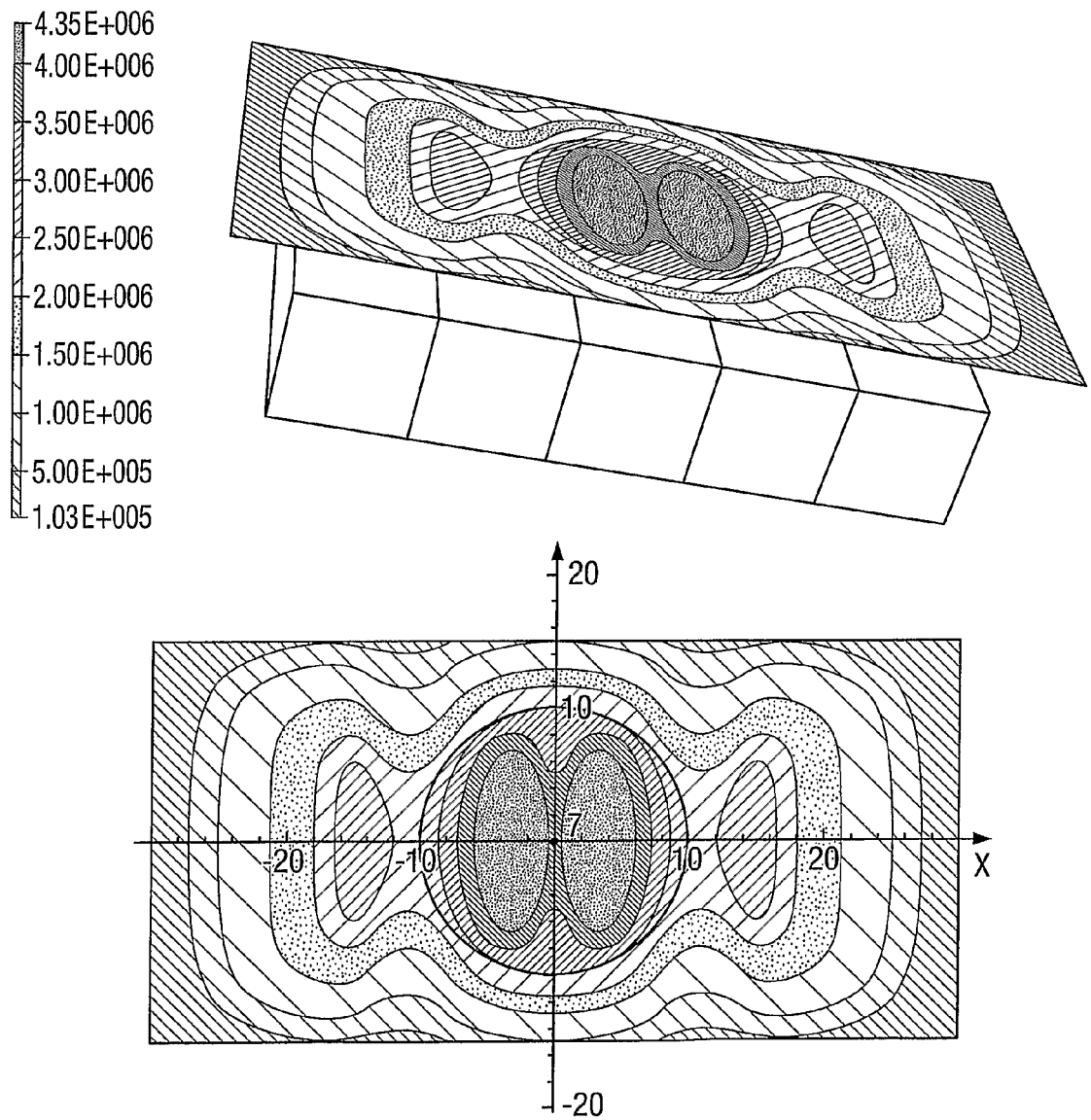

FIG. 14 is a contour map showing the forces per volume in T·A/$m^2$ (N/$m^3$) on a plane 5 mm above a Halbach array, which have been calculated using finite element modelling methods.

Figure 15:
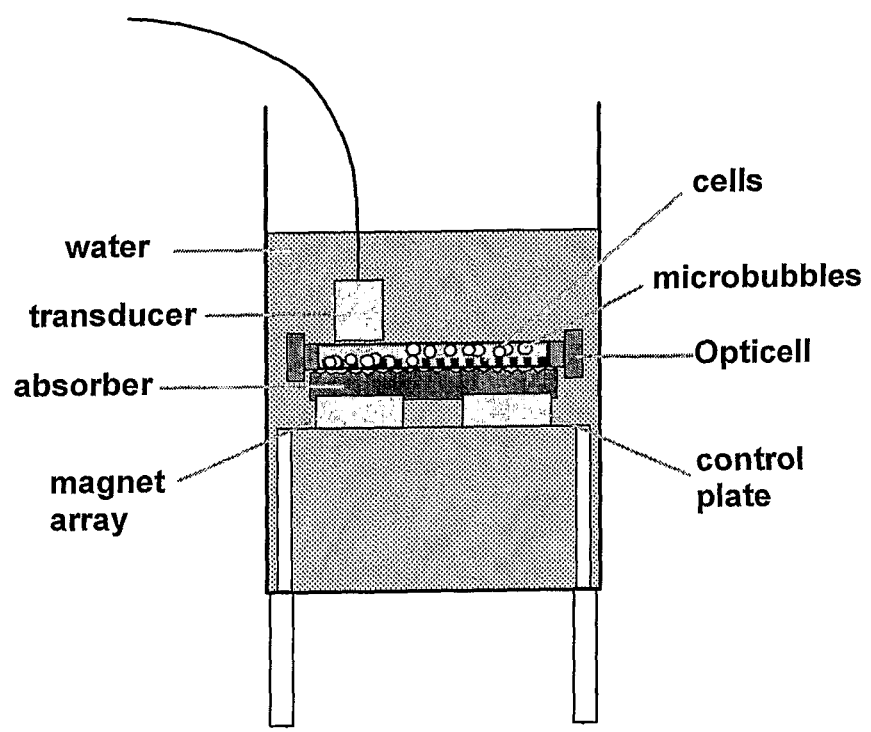

FIG. 15 is a schematic diagram showing the experimental apparatus that was used to perform cell transfection experiments. The diagram also illustrates the idealised situation where magnetically actuated microbubbles are drawn towards a cell monolayer on the bottom surface of the OptiCell™.

Figure 16:
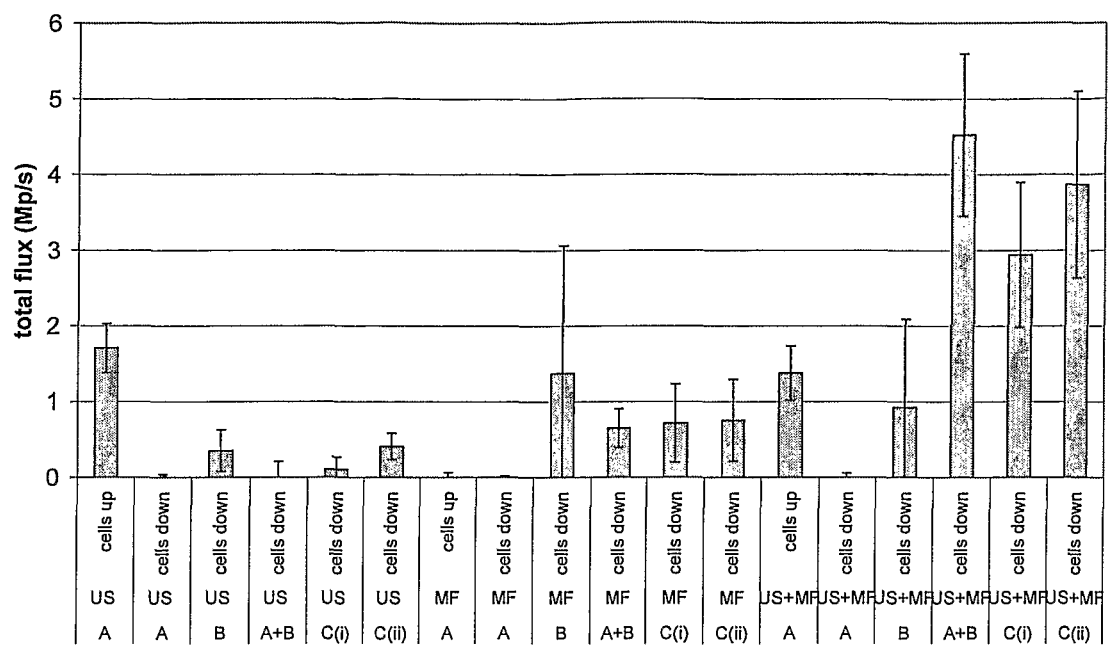

FIG. 16 is a histogram showing the experimental results for Luciferase expression with different bubble preparations and exposure conditions (error bars indicate standard deviations).

Figure 17:
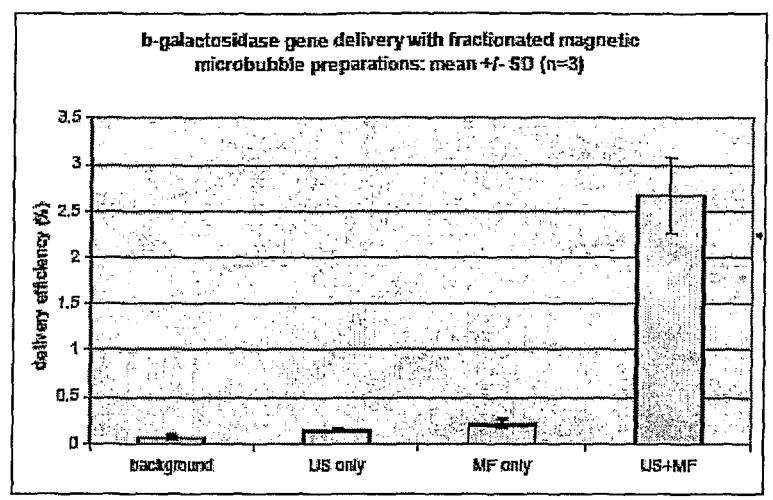

FIG. 17 is a histogram showing the experimental results for β-galactosidase expression with different preparations and exposure conditions (error bars indicate standard deviations).

Figure 18:
Figure 18:
Figure 18:
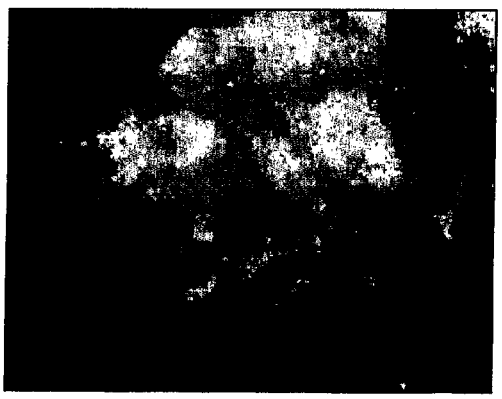
Figure 18:

FIG. 18 shows the experimental results for FITC-dextran delivery with bubble preparation C(ii) under different exposure conditions.

OPTIMISATION OF A MICROBUBBLE DESIGN

In order to determine the parameters of a microbubble structure or design, which is optimised for magnetic actuation in a liquid and is to be ruptured by ultrasound, then the equations describing the microbubble need to be considered. Some of these equations may constrain the design of the microbubble and are considered below.

1. Microbubble Buoyancy

The weight of an individual microbubble, W, is given by $$W = -\frac{4}{3}\pi g[\rho_g R_1^3 + (R_2^3 - R_1^3)((1-\alpha)\rho_0 + \alpha\rho_{np})]$$

and the buoyant force $F_{BW}$ of the microbubble in a liquid, such as water, is given by $$F_{BW} = \frac{4}{3}\pi g \rho_l R_2^3$$

where g is acceleration due to gravity, $\rho_g$, $\rho_0$, $\rho_{np}$, and $\rho_l$ are the densities of the filling gas (gas core of the microbubble), the nanoparticle suspending liquid of the microbubble shell, the nanoparticle material and the carrier liquid (i.e. the liquid in which the microbubble is to be suspended in use) respectively and α is the volume fraction of nanoparticles in the shell. The outer layer of the shell that surrounds the solvent layer, such as the phospholipid coating shown in FIG. 1, has a relatively negligible thickness (~1.5 nm) and its contribution to the weight of the microbubble may be neglected.

2. Magnetic Force

The force on an individual magnetic microbubble on application of a magnetic field may be represented by:

$$F_M = -\frac{4\pi\chi(B\cdot\nabla)B\alpha(R_2^3 - R_1^3)}{3\mu_0}$$

where B is the magnetic flux or field strength at the location of the microbubble, χ is the effective volumetric susceptibility of the magnetic nanoparticles suspended in the solvent layer, and $\mu_0$ is the permeability of free space.

3. Acoustic Excitation and Scattering

When a microbubble is exposed to ultrasound, it undergoes volumetric oscillations. The enhancement in cell membrane permeability that is observed for non-magnetic microbubbles is thought to be related to the volumetric oscillations of the microbubbles. The amplitude of these oscillations must therefore be sufficient to promote transfection enhancement.

The equation of motion describing microbubble oscillations is non-linear (Stride, E; Phil. Trans. Roy. Soc. A., 2008, 366, 2103-2115), but a linearised form can be written as:

$$m\ddot{x}+b\dot{x}+kx=p(t)$$

where $p(t)=p_{inc}\sin(\omega t)$ and $p_{inc}$ is the pressure amplitude of the applied ultrasound field and ω is its frequency in radians/s. The instantaneous radius of the bubble R is given by $R=R_{01}x(t)$, where $R_{01}$ is the initial value of the radius of the gas core and x(t) represents a small change in R.

The coefficients m, b and k are given by:

$$m = \rho_s R_{01}^2\left(1 + \frac{R_{01}(\rho_s - \rho_l)}{R_{02}\rho_s}\right)$$

$$b = \frac{4}{R_{02}^3}\left(\mu_l R_{01}^3 + \mu_s\frac{4}{3}\pi(R_{02}^3 - R_{01}^3) + \frac{R_{01}^3}{R_{02}}\eta_{s0}\right)$$

$$k = 3\kappa\left(p_0 + \frac{2\sigma_{01}}{R_{01}} + \frac{2\sigma_{02}}{R_{02}}\right) + \frac{4K\Gamma_0^{\gamma+1}R_{01}^3}{R_{02}^4(\gamma+1)} - \frac{2\sigma_{01}}{R_{01}} + \frac{2\sigma_{02}R_{01}^3}{R_{02}^4}$$

where $\rho_s=((1-\alpha)\rho_o+\alpha\rho_{np})$ is the effective density of the liquid layer around the bubble, $\mu_s$ is its effective viscosity, $\mu_l$ is the viscosity of the liquid in which the bubble is suspended and $\eta_{s0}$ is the viscosity of the outer coating layer, such as a surfactant. κ is the polytropic constant for the gas core, $p_0$ is the ambient pressure, $\sigma_{01}$ and $\sigma_{02}$ are the initial interfacial tensions at the inner and outer surfaces of the liquid layer. $\Gamma_0$ is the initial concentration of the material that forms the outer coating layer (e.g. surfactant on the bubble surface), y and K are constants for the material that forms the outer coating layer and $R_{02}$ is the initial radius of the microbubble.

Solving equation of motion in linearised form above, the amplitude of radial oscillation of the bubble, X, can be estimated as $$X = \frac{p_{inc}}{\sqrt{((k-m\omega^2)^2 + b^2\omega^2)}}$$

Similarly, the scattering cross-section which determines whether or not microbubbles can be detected from the scattered ultrasound field that they produce can be written as $$\sigma_{scat} = \frac{4\pi\omega^4 X^2 \rho_w^2 R_{01}^6}{p_{inc}^2}.$$

4. Viscous Drag

The viscous drag force on a microbubble suspended in a liquid having a net flow of velocity u is given by $$F_D = \frac{u^2 C_D \pi R_{02}^2}{2}$$

and for a low velocity (laminar) flow $$F_D = 6\pi\mu_l u R_{02}$$

where $C_D$ is the drag coefficient (approximation for a solid sphere) and $\mu_l$ is the viscosity of the liquid.

Parameters for Optimum Microbubble Designs

Whilst it is desirable to increase the magnitude of the magnetic force on an individual microbubble by increasing its magnetic nanoparticle content, there will be a maximum volume fraction of nanoparticles that can be suspended in the shell before precipitation of the nanoparticles occurs. Moreover, the volume fraction cannot increase indefinitely because the viscosity of the liquid in which the nanoparticles are suspended will become so high that it will effectively be a solid. Thus, a first condition that influences the microbubble design is that the volume fraction α of magnetic nanoparticles in the solvent layer of the microbubble shell is $$0 < \alpha < 0.2. \quad (i)$$

In order that the magnetic microbubbles are directable and actuatable in the environment of use, the microbubbles must contain sufficient magnetic material to enable them to be actuated by an applied magnetic field. Further, the force provided by this field must be sufficient to overcome microbubble weight and the microbubble buoyancy. A second condition that determines the microbubble design is that:

$$|F_M| > |F_{BW} + W|. \quad (ii)$$

Microbubbles having marginal buoyancy are more responsive to the applied magnetic field because they neither sink nor rise rapidly. A third condition that influences the design of the microbubble is that:

$$-1 < \frac{F_{BW} + W}{W} < 0 \text{ as above.} \quad (iii)$$

If the microbubble is initially introduced away from the target site, then ideally it should be moveable toward the target site using a magnetic field. As the bubble moves through the liquid in which it is suspended, it will experience drag resistance from the viscosity of the liquid and the flow of that liquid. A fourth condition is that magnetic actuation of the microbubble should be sufficient to overcome the drag force of the microbubble in the carrier liquid, such that:

$$|F_M| > |F_D|. \quad (iv)$$

It is preferable that the microbubble is able to be monitored using ultrasound. The microbubble must, however, be capable of being ruptured when exposed to high intensity ultrasound at a practicable frequency that can be generated by available apparatus. As explained above, the uptake of a therapeutic agent by cells is improved by sonoporation. The microbubble must therefore contain a sufficient volume of gas in order that it can undergo volumetric oscillations of sufficient amplitude in response to an ultrasound field. A fifth condition is therefore that the microbubble scattering cross section satisfies the condition:

$$\sigma_{scat} \geq \frac{4\pi\omega^4 \rho_l^2 R_{01}^6}{((k - m\omega^2)^2 + b^2\omega^2)}; \quad (v)$$

where $m = \rho_l R_{01}^2$, $$b = 4\mu_l + \frac{3.6 \times 10^{-8}}{R_{01}} \text{ and } k = 3 \times 10^5 + \frac{0.24}{R_{01}}.$$

(ω is the frequency of the ultrasound, $\rho_l$ is the density of the carrier liquid, $R_{01}$ is the initial radius of the gas core of the microbubble and $\mu_l$ is the viscosity of the carrier liquid (the liquid in which the microbubble is suspended)).

If the microbubbles are to be administered intravenously, then the microbubbles must not be too large, otherwise the amount of gas introduced into the blood stream might be harmful and cause an embolism. Thus, there is a maximum diameter of the microbubbles for in vivo applications, which, generally in practice, should not exceed 8 μm.

Determination of Optimum Microbubble Design Parameters

By applying each of the above conditions, a range of microbubble designs can be determined that are optimised for delivery of a therapeutic agent or for cell transfection applications, when used with a magnetic field of known strength, ultrasound of a known frequency and the flow velocity in the carrier liquid is known. A range of optimised microbubble designs may be determined from the parameters ψ, ϕ and λ, which are defined below.

ψ is defined as:

$$\psi = \frac{F_{BW} + W}{W} = 1 - \frac{\rho_l R_2^3}{(\rho_g R_1^3 + (R_2^3 - R_1^3)((1-\alpha)\rho_0 + \alpha\rho_{np}))}.$$

For marginally buoyant microbubbles (i.e. when $|W| < F_{BW} < |2W|$) ψ is between 0 and −1.

ϕ is defined as:

$$\varphi = \frac{F_M}{F_{BW} + W} = \frac{-\chi(B \cdot \nabla)B\alpha(R_2^3 - R_1^3)}{g\mu_0\{\rho_l R_2^3 - (\rho_g R_1^3 + (R_2^3 - R_1^3)((1-\alpha)\rho_0 + \alpha\rho_{np}))\}}.$$

For microbubbles to be actuatable by an applied magnetic field it is necessary that ϕ is less than −1.

λ is defined as:

$$\lambda = \frac{F_M}{|F_D|} = \frac{-2\chi(B \cdot \nabla)B\alpha(R_2^3 - R_1^3)}{9\mu_l R_2 \mu_0 |u|}.$$

In order that the microbubbles are responsive and moveable in the carrier liquid when a magnetic field is applied, the magnetic force must be sufficient to overcome the drag viscosity of the microbubble in that liquid. Thus, the parameter λ should be less than than −1.

As an example, an optimised microbubble formulation was determined using the parameters set out in Table 1. A graph of shell thickness as a fraction of gas core radius against nanoparticle volume fraction was plotted for each of ψ, ϕ and λ, with ψ, ϕ and λ each taking various values, see FIGS. 2 to 4. The highest value shown on the x-axis of each graph is 0.2 to represent the condition that $0 < \alpha < 0.2$.

TABLE 1

| Parameter | Value |
| --- | --- |
| $\rho_l$ (liquid = water) | 1000 kg/m³ |
| $\mu_l$ (liquid = water) | 0.001 Pa s |
| $\rho_g$ (gas = air) | 1.24 kg/m³ |
| g | 9.81 m/s² |
| $p_0$ | 10⁵ Pa |
| $\rho_0$ (isoparaffin) | 700 kg/m³ |
| $\rho_{np}$ (iron oxide) | 5100 kg/m³ |
| nanoparticle radius | 5.00 × 10⁻⁹ m |
| $\mu_0$ | 1.26 × 10⁻⁶ Tm/A |
| χ for B = 0.4 T | 0.089 |

In FIG. 2, there are lines for $\psi=0$ and $\psi=-1$. These lines represent the limits for microbubbles that satisfy the conditions for $\psi$ set out above. The region between the lines for $\psi=0$ and $\psi=-1$ therefore represents the range of microbubble formulations that satisfy the $-1<\psi<0$.

Similarly, FIGS. 3 and 4 show the limits for the parameters $\phi$ and $\lambda$ that satisfy the condition $\phi<-1$ and $\lambda<-1$ for a given magnetic field and flow velocity of the liquid in which the microbubbles are suspended (in this case, $(B \cdot \nabla)B=18$ T$^2$/m and a flow velocity of water of $10^{-4}$ m/s).

A formulation map (FIG. 5) may be obtained by combining on a single graph, the individual graphs for $\psi$, $\phi$ and $\lambda$, such as those shown in FIGS. 2 to 4. The formulation map defines a range of microbubble formulations that satisfy the conditions set out above for each of $\psi$, $\phi$ and $\lambda$. The inventors have surprisingly found that the requirement that the magnetic microbubbles are marginally buoyant (represented by the conditions for parameter $\psi$) constrains the design of a microbubble for the applications described herein.

It is desirable that the values of $\alpha$ and the shell thickness as a fraction of gas core radius ($\xi$) are as small as possible, whilst still satisfying the limits set out for $\psi$, $\phi$ and $\lambda$. For example, using the formulation map in FIG. 5, it can be seen that a microbubble having a volume fraction of magnetic nanoparticles of 0.1 and a gas core radius of 1 µm can have a shell thickness of approximately 0.23 µm for the magnetic field and flow velocity in water specified above.

Experimental Details

Microbubble Preparation

A microbubble suspension was prepared based on a determination of the maximum shell thickness using the method described above, for a specific quantity of magnetic nanoparticles and so that the microbubbles had a gas content suitable for excitation at 1 MHz and were able to be magnetically actuated in the magnetic field that was to be used. There was no liquid flow velocity in the cell transfection experiments below.

The processing steps (sonication time, power etc.) were optimised empirically to obtain a suspension comprising the optimised microbubbles. In order to determine the efficacy of the magnetic microbubbles in the presence of an ultrasound and/or a magnetic field, a series of different microbubble/nanoparticle suspensions were prepared for comparison.

A. Phospholipid Microbubbles 15 mg of hydrogenated L-α-phosphatidylcholine (Sigma Aldrich, Poole, UK) was added to 15 ml of aerated phosphate-buffered saline (PBS) at 4° C. Initial mixing to disperse the phospholipid was by sonication for 30 s using an ultrasonic cell disruptor (XL2000, probe diameter 3 mm, Misonix Inc., Farmingdale, N.Y., USA) operating at 22.5 kHz and level 4 corresponding to 8 WRMS output power. The probe was raised and lowered to and from the liquid surface in order to entrain gas. Following sonication the mixture was immediately manually shaken vigorously for 30 s.

B. Magnetic Micelles 15 mg of hydrogenated L-α-phosphatidylcholine phospholipid was added to 15 ml of (unaerated) PBS at 4° C. and sonicated at level 4 for 30 s. The probe was held within the liquid and without any manual shaking. 15 µl of a suspension of 10 nm diameter magnetic nanoparticles in isoparaffin (Liquids Research, Bangor UK) were then added and the mixture sonicated again under the same conditions.

C. Magnetic Microbubbles

The steps listed above for A were repeated, but with two separate sonication stages were performed and 15 µl of the magnetic suspension was added prior to the second sonication. This resulted in the preparation of an initial suspension of microbubbles, which is referred to herein as C(i).

A subfraction suspension of microbubbles C(ii) was prepared by removing 5 ml of the C(i) suspension to a syringe with a tap and the subfraction was then left to settle for 30 min. After this time, the tap was opened to remove 4 ml from the lower part of the suspension. The remaining 1 ml, corresponding to a clearly separated layer, was used for the experiments. An upper layer consisting of relatively large bubbles (~0.1 mm) that could not be removed from the syringe via the tap was discarded.

D. SonoVue™ Microbubbles

For comparison, a suspension of a commercially available ultrasound contrast agent, SonoVue™ (Bracco Milan, Italy) was prepared according to the manufacturers instructions.

Characterisation of Microbubbles

1. Macroscopic Observations

Upon standing after processing, the separation of the different preparations into distinct layers was observed as shown in FIG. 6 after 15 minutes and 30 minutes. In both the diluted and undiluted suspensions, the phospholipid only microbubbles (A) rapidly separated into a frothy layer of relatively large bubbles above an opaque layer of microbubbles, as determined by optical microscopy. The magnetic micelles (B) did not separate into distinct layers, although there was a vertical gradation in colour, which indicated that there was some settling of magnetic material on the bottom of the vial. As for A, the diluted and undiluted magnetic microbubble preparation (C(i)) separated into a white frothy layer above an opaque layer. In this case, however, the opaque layer was dark brown indicating the presence of magnetic material, which persisted even after the preparation was allowed to stand for several hours. This was confirmed by testing the response to magnetic actuation (FIG. 7). It was this subfraction of C(i) that was removed as described above and used in the experiments as preparation C(ii). Some sedimentation of magnetic material on the bottom of the vial was also observed.

2. Optical Microscope Observations

Each suspension was examined using an optical microscope in a haemocytometer to determine the average size and concentration of microbubbles/micelles present. In the case of the magnetic bubbles, their response to magnetic actuation was also examined. Microscopic images were captured using a digital camera linked to a computer.

Microscopic observations of preparation A (sample taken from below the frothy layer) indicated the presence of highly refractile, gas-filled bubbles similar in appearance to those in the suspension of commercial contrast agent SonoVue™, although with a somewhat broader size distribution and lower concentration, as indicated in Table 2. Preparation C(i) was also seen to contain microbubbles that were similar in appearance, although smaller in size to those in A (see FIG. 8), together with smaller, brown spherical particles (~1-2 µm in diameter) and less refractile sub-micron sized particles. When a single bar magnet was held nearby, there was seen to be little movement of the "A-type" microbubbles, but the other particles were seen to stream towards the magnet (see FIG. 9) with the smallest particles rapidly forming chains which were seen to reorientate when the magnet was moved.

The microbubble and nanoparticle suspensions that were prepared are set out in the Table below. Due to the inherent uncertainty associated with automated particle counting methods for microbubbles, the concentration of the different preparations was estimated by direct counting from the microscopic images and is consequently only approximate.

TABLE 2

| Preparation | Composition | Diameter range (μm) | Concentration (bubbles/ml) |
|---|---|---|---|
| A | Phospholipid coated microbubbles | 1-50 | $5 \times 10^7$ |
| B | Magnetic micelles (no gas) | 1-2 | $5 \times 10^7$ |
| A + B | Bubbles + micelles (combined by mixing after preparation) | as above | as above |
| C(i) | Magnetic microbubbles prepared from phospholipid and magnetic fluid (mixed prior to sonication) | 1-5 | $5 \times 10^7$ |
| C(ii) | Subfraction of C(i) | 1-2 | $5 \times 10^7$ |
| D SonoVue ™ | Commercially available phospholipid coated microbubbles (ultrasound contrast agent) | 1-20 | $1 \times 10^8$ |

3. Ultrasound Characterisation

Measurements of the attenuation and phase velocity of ultrasound through the diluted microbubble suspensions were made using standard apparatus, such as that described by Stride & Saffari (IEE Transactions in Ultrasonics, Ferroelectrics & Frequency Control; 2005, 52(12): 2332-45). The measurements confirmed the presence of gas-filled bubbles in the preparation.

FIGS. 10 to 12 show that the magnetic microbubble preparation C(i) was found to have comparable echogenicity to the commercially available SonoVue™ microbubbles, i.e. similar levels of ultrasound attenuation were observed. In contrast, the attenuation through the initial mixture of phospholipid and magnetic nanoparticles prior to shaking and sonication, and through preparation B, was found to be negligibly different from water. This confirmed the presence of gas-filled bubbles in C. It should be noted that FIG. 12 shows that the frequency response of the magnetic microbubbles was different from that of SonoVue™, with a pronounced peak at approximately 4 MHz. Similarly, FIGS. 10 and 11 indicate that there was not a noticeable change in the speed of ultrasound through the suspension, as was observed for SonoVue™. These observations can probably be attributed to the different concentration and size distribution of the SonoVue™ microbubbles (see Table 2).

Magnetic Actuation of Microbubbles

The force over a magnetic particle of volume V is given by $$F_m = \frac{V\chi}{\mu_0}(B \cdot \nabla)B = V\chi\mu_0(H \cdot \nabla)H,$$

where $\chi$ is the volumetric susceptibility ($\chi=M/H$), $\mu_0$ is the permeability of vacuum ($\mu_0=4\pi\times10^{-7}$ Tm/A), B is the magnetic flux and H is the magnetic field.

1. Analysis of Magnetic Content of the Microbubbles

The magnetic content of the microbubbles was analysed using a Faraday yoke, which allows the application of a force such that the product (B·∇)B is constant. The Faraday yoke is a device that consists of a horseshoe electromagnet where the poles are arranged in a manner such that in the gap between the poles the product (B·∇)B is constant.

The magnetic force on the microbubbles is compensated by the drag force acting on them in the opposite direction. The drag force is described by the Stokes law:

$$F_d = -6\pi\eta r v,$$

where r is the bubble outer radius, $\eta$ is the fluid viscosity (in this case it is $\eta_{dH2O}=10^{-3}$ kg·m/s) and v the bubble velocity. Assuming equilibrium conditions where $F_m+F_d=0$, then the velocity is given by $$v = \frac{V\chi(B \cdot \nabla)B}{\mu_0 6\pi\eta r}$$

Figure 1:
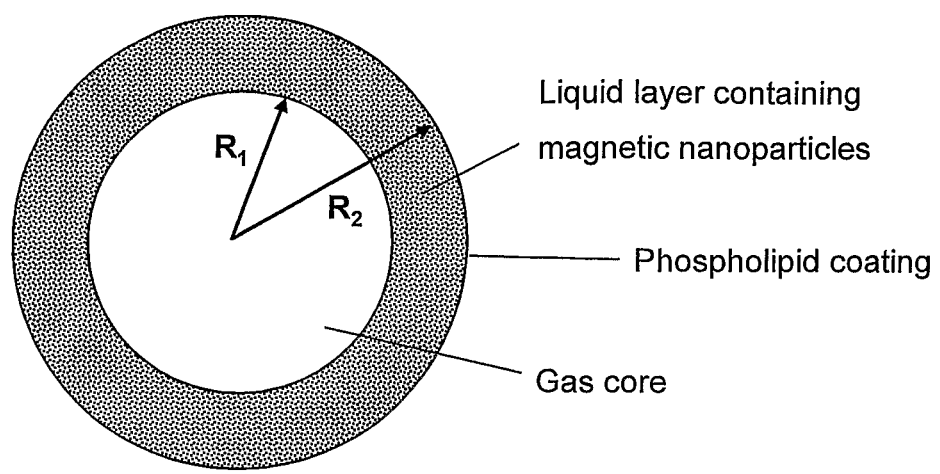
FIG. 1 is a schematic cross-section of an embodiment of a magnetic microbubble, which has a phospholipid coating.

The susceptibility $\chi$ of the commercial magnetic ferrofluid used as the coating (http://www.liquidsresearch.com/products/ferro_sink.asp) was calculated from an M-H curve, where magnetisation (M) is plotted as a function of applied field (H), using a SQUID magnetometer (FIG. 1). In SI units, $\chi=4\pi$ M [emu/cc]/H [Oe]. At H=1000Oe we have $\chi=0.28$. The magnetic shell volume in equation above is given by $$V = \frac{4}{3}\pi(R_2^3 - R_1^3),$$

where $R_2$ and $R_1$ are the radius of the microbubble and the radius of the gas core respectively.

The velocities were calculated by placing the yoke on a microscope (Nikon Diaphot, 10× objective, 10× eyepiece amplification) so that the trajectories of the bubbles could be recorded with a video camera. The area observed in the image from the camera corresponds to 257×274 microns of the sample. Approx. 15 μl of a dH$_2$O suspension of the bubbles was placed in the gap of the yoke in a well made of a 1 cm diameter microscope slide and a plastic washer of 10 mm outer and 6 mm inner diameter on top of it. The current in the coil of the yoke was switched on (1.05 A) and the bubbles moved in the direction of the force. For this current the product (B·∇)B equals 0.143 T$^2$/m, as calibrated and verified by the model. For a typical microbubble with a magnetic shell of 5.55·10$^{-18}$ m$^3$ (3 μm sized bubble with a 50 nm thick magnetic shell), this corresponds to a force of 0.55 pN. The trajectories of the bubbles are recorded in the video camera and the velocities calculated by measuring in the screen the distance traveled during 18 seconds. The experiment shows that the microbubbles could be actuated on a time frame that is suitable for in vivo use.

2. Magnetic Actuation of the Microbubbles in the Delivery Experiments

A Halbach array was used to attract the microbubbles towards the cells in the delivery experiments described below. A Halbach array is an arrangement of permanent magnets where the permanent magnetisations are turned at an angle from one magnet to the next. The advantages of this configuration over a simple permanent magnet is that it allows the application of forces that are 3 times larger and that it creates a field that is homogeneous in the plane of the cells. The array is composed of 5 square cross-section NdFeB magnets of 25×10×10 mm (Neotexx, Germany) with transversal magnetisation ($B_r$=1.50 T) turned 90° from one magnet to the next. They are inserted in an aluminium frame so that the total horizontal area of both the array-frame is 65×28 mm.

From Finite Element Modelling (Vector Fields, Oxford) the forces per volume on a plane 5 mm above the array have been calculated. As shown in FIG. 14, the forces are quite homogeneous in the area of the transducer (circular area of 20 mm in diameter), with a mean value of $4.2 \cdot 10^6$ T·A/m² (4.2 N/m³). For example, for a typical microbubble with a magnetic shell of $5.55 \cdot 10^{-18}$ m³ (3 micron sized bubble with a 50 nm thick magnetic shell), this corresponds to a magnetic force of 23 pN.

Method of Performing Delivery Experiments

1. Cell Culture

Chinese hamster ovary (CHO) cells were grown in OptiCell™ (BioCrystal Inc., Westerville, Ohio, USA) cell-culture devices: cells were seeded in 10 ml Dulbecco's Modified Eagle's Medium (DMEM) with 10% fetal calf serum (FCS) the day before the delivery experiment and grown at 37° C. under 5% $CO_2$, in order to reach ~80% confluence for experimental use.

2. Delivered Molecules

Delivery experiments were carried with three different types of molecule to determine if the microbubbles could enhance transfection for a range of molecule sizes. These are summarised in Table 3.

TABLE 3

| Molecule type | Relative molecular mass (kDa) |
|---|---|
| pLuc plasmid DNA | 5000 kDa |
| β-galactosidase plasmid DNA | 5000 kDa |
| FITC-Dextran | 500 kDa |

The majority of the experiments were carried out with plasmid DNA encoding firefly luciferase, as this offered the most convenient means of quantitatively assessing transfection. Prior to experimental use, the medium in each OptiCell™ was replaced with 9.6 ml OptiMEM serum-free medium (Invitrogen) containing 50 μg pLuc plasmid DNA, following which the cells were returned to the incubator until microbubble addition and ultrasound exposure. This plasmid encodes fire-fly luciferase under the control of the CMV promoter, enabling delivery and expression in cells to be detected by monitoring light emission upon addition of the substrate luciferin. Chemically competent DH5α *Escherichia coli* (Invitrogen) were transformed and resultant cultures were grown in the presence of 100 μm/ml ampicillin. pLuc was extracted and purified using a QIAfilter Maxiprep Kit (Qiagen, Crawley, UK). Plasmid concentration (typically 1 mg/ml) and purity (ratio of optical densities at 260 nm and 280 nm of 1.7-1.9) were evaluated using spectrophotometry.

A series of experiments were performed where the method above was repeated, except that the Luc plasmid DNA was replaced with either (i) 50 μg plasmid DNA encoding β-galactosidase; or (ii) 1 mg/ml, 0.1 mg/ml, and 0.01 mg/ml (2 μM) FITC-Dextran (Mr 500 kDa).

3. Microbubbles

Bubble preparation took place typically ~1 hour prior to the transfection tests in order to minimise the effects of changes in bubble size, concentration etc. over time. For each test, 0.4 ml of the appropriate preparation (lipid-only, SonoVue™, magnetic microbubbles or magnetic micelles) was added to the OptiCell™ immediately prior to its placement in the water tank (see below) for sham, ultrasound and/or magnetic field exposure. One minute of settling and temperature equilibration time (in the presence of the magnetic field, when used) was allowed before ultrasound exposure.

For the luciferase experiments, each of the different bubble preparations (Table 2) were tested separately with sham, ultrasound and/or magnetic field exposure and with cells on both the upper and lower OptiCell™ membranes. For the subsequent delivery experiments (β-galactosidase and FITC-Dextran), only preparation C(ii) was used, with either sham or combined ultrasound/magnetic field exposure and with the cells on the lower membrane of the OptiCell™.

4. Magnetic Field

As discussed in the section on magnetic actuation of microbubbles above, the magnetic force was provided by a Halbach array consisting of 5 NdFeB permanent magnets with transversal magnetisations orientated at angles of 90° from one to the next in an aluminium frame which was placed underneath the OptiCell™ plate with 3 mm separation between the magnet surface and the lower OptiCell™ membrane. As it was necessary for the Halbach array to be in close proximity to the cells, it was not possible to use an acoustic absorber, as described in an experimental set up in the prior art (Rahim et al; Ultrasound Med. Biol., 2006; 32(8): 1269-79). The surface of the array closest to the transducer was therefore covered with a layer of textured putty (3 mm thick) in order to minimise ultrasound reflections.

For the experimental conditions involving no magnetic field, an aluminium metal bar was substituted for the array so that any effects on the ultrasound field would be comparable. The cells were adherent to either the upper or lower membrane of the OptiCell™, which was placed on the putty, such that the magnetic field would counteract the effect of buoyancy upon magnetic bubbles and, respectively, draw them away from or towards the cell monolayer. For the sake of efficiency, the array and control were used together, placed at opposite ends of a single OptiCell™ (see FIG. 15).

5. Ultrasound Exposure

Ultrasound exposure was performed using an apparatus described in the prior art (Rahim et al; Ultrasound Med. Biol., 2006; 32(8): 1269-79) and as shown in FIG. 15. The OptiCell™ was suspended horizontally, resting on the magnet array with overlying putty absorber, in a custom built water tank; temperature was maintained at 37° C. by means of a heat-exchanger and externally heated water bath controlled by a thermocouple suspended in the tank. Ultrasound excitation 1 min later was provided by a spherically focused single element piezoelectric transducer (custom-made by Imasonic, Besancon, France) which was placed on the upper membrane of the OptiCell™ (care was taken to avoid trapping any air between the transducer and the membrane) so that the contents were in the near field of the transducer. The nominal centre frequency of the transducer was 1 MHz with 68% bandwidth. The diameter was 20 mm and the radius of curvature 67 mm. The acoustic field in this position has been measured and determined to be homogeneous (Rahim et al; Ultrasound Med. Biol., 2006; 32(8): 1269-79).

The transducer was excited by a 40 cycle 1 MHz sinusoidal pulse from an arbitrary waveform generator (model 33220A, Agilent Technologies Inc., Loveland, Colo., USA), which was fed to the transducer via an RF power amplifier (58-dB gain, model BT00500 BETA, Tomco Technologies, Norwood, Australia). The pulse repetition frequency was 1 kHz and the pulse burst time was 10 s. The outputs from the signal generator and amplifier were sampled using a digital oscilloscope (Picoscope, Pico Technology Ltd., St. Neots, UK). The acoustic pressure generated was 0.5, 1, or 2 MPa (peak to peak), but the experiments used a value of 1 MPa.

For sham exposure to ultrasound, the transducer was placed on the OptiCell™ but not excited.

6. Cell Imaging

Following ultrasound and/or magnetic field exposure, the cells were incubated for 24 hours and then examined. To eliminate the risk of delayed toxicity associated with prolonged exposure to the microbubbles, the medium was replaced 30 min after gene delivery with 10 ml fresh DMEM/FCS growth medium. All cells were confluent and healthy at the time of evaluating expression, indicating no ill effects of the experimental procedures.

For the luciferase experiments, expression was evaluated using an IVIS camera (Xenogen Corporation, California) 2 hours after replacement of the medium with OptiMEM containing 15 µg/ml luciferin and further incubation at 37° C. Light was captured during a 1 min exposure, at 37° C., on the highest sensitivity setting. Regardless of the orientation of the cells for the delivery step of the experiment, all OptiCells™ were imaged with the cells uppermost (towards the CCD camera). Images were analysed using the manufacturer-supplied Living Image software.

For the β-galactosidase experiments, cells were fixed at 24 h with 0.5% glutaraldehyde for 15 min prior to histochemical staining for enzyme activity. For the FITC-dextran experiment, sections of the OptiCell™ membrane were cut from centre of insonation (or mock insonation) zones and inverted on glass slides using Dako fluorescent mounting medium. Wrapped and stored in fridge overnight before fluorescence microscopy using x63 oil immersion lens on Zeiss Axioplan2 with Axiovision software capture.

Results of Delivery Experiments

1. Luciferase Expression

The results are shown in FIG. 16. There was found to be negligible transfection in the OptiCells™ that were exposed to ultrasound and/or the magnetic field in the absence of microbubbles and/or magnetic micelles, indicating that the intensity of the ultrasound field was insufficient to produce significant cavitation activity in the absence of preformed microbubbles.

The bubbles coated with phospholipid only (preparation A) did promote transfection with ultrasound exposure when the cells were on the upper surface of the OptiCell™ but significantly less (approx. 10 times) when the cells were on the lower surface (see FIG. 16). This was in agreement with previous results obtained for commercial ultrasound contrast agent microbubbles (SonoVue™, Bracco, Milan Italy) (Rahim et al; Ultrasound Med. Biol., 2006; 32(8): 1269-79) and confirmed the importance of proximity between the cells and the microbubbles, in this case produced by buoyancy. As would be expected, the presence of the magnetic field was found to have little effect upon transfection with the phospholipid only bubbles. Similarly, there was no transfection with the sham exposure.

A suspension of magnetic nanoparticles alone was found to produce a very small amount of transfection when the cells were on the lower surface of the OptiCell™ and exposed to both ultrasound and the magnetic field. The effect was inconsistent between tests however.

The magnetic micelles particles (B) were found to be more effective for both ultrasound and magnetic field exposure (with the cells on the lower surface), but the total flux was low compared to that produced by preparation A with the cells on the upper surface (see FIG. 16). Interestingly, there was found to be little difference between the results for ultrasound exposure alone and for ultrasound exposure with the magnetic field (FIG. 16). Transfection under sham exposure to ultrasound and/or the magnetic field was found to be negligible with both the nanoparticles and the micelles.

The combination of the phospholipid only bubbles and the magnetic micelles (A+B) produced little activity when exposed to ultrasound alone with the cells on the lower surface. As might be expected, the total flux was similar to that observed with B. With exposure to both ultrasound and the magnetic field; however, significant transfection was observed (FIG. 16).

With preparation C(i), relatively low levels of transfection were observed with the cells on the lower surface exposed to ultrasound only (FIG. 16) and slightly higher levels with the application of the magnetic field only. Simultaneous exposure, however, resulted in significant activity (FIG. 16).

C(ii) produced qualitatively similar results but the total flux levels were quantitatively much higher. Moreover, in this case, transfection due to the magnetic field alone was approximately equal to that produced by ultrasound alone.

2. β-Galactosidase Expression

Similar results were obtained with the β-galactosidase experiments, as shown in FIG. 17. Delivery efficiency for microbubble preparation C(ii) was found to be approximately three times higher than for C(i).

3. FITC-Dextran Delivery

The FITC-Dextran experiments also indicated that combined exposure to ultrasound and the magnetic field enhanced transfection (FIG. 18) and that the microbubble preparation C(ii) was again more effective than C(i). As shown, adherence of the Dextran to the cells was observed in all cases but only with combined exposure was there evidence of cell uptake. This demonstrated that the magnetic microbubbles were effective in transfecting a range of different molecule sizes.

4. Conclusion

Preparations A+B and C(ii) were found to be most effective at promoting transfection of pLuc plasmid DNA when exposed to both ultrasound and the magnetic field. This indicates that C(ii) consisted predominantly of microbubbles whose coatings contained magnetic material. The bubbles were thus drawn down on to cells by the force from the magnetic field and the increased proximity resulted in increased transfection, i.e. it produced a similar effect to that observed with A as a result of buoyancy. Observation of the microbubbles under an optical microscope supported this hypothesis, as the bubbles were different in appearance from those in A and were seen to translate in response to an applied magnetic field. The fact that preparation C(ii) was found to be more effective than C(i) also supports this, since microbubbles coated with a relatively dense layer in addition to phospholipid would have been more buoyant than magnetic micelles and/or uncombined magnetic nanoparticles, but less so than bubbles coated with phospholipid only. Thus, by drawing off the subfraction just below the top layer of preparation C(i), C(ii) would have contained a higher concentration of magnetically active microbubbles (rather than a mixture of particles), which would have undergone more interactions with the cells and hence promoted more transfection.

The existence of a second mechanism is indicated by the fact that the combination of phospholipid only bubbles (A) and magnetic micelles (B) also produced enhanced transfection. As shown in FIG. 16, in the absence of any magnetic material, preparation A produced negligible transfection when the cells were on the lower surface of the OptiCell™. Thus, the results for A+B were expected to be similar to those for B alone (FIG. 16) and it was surprising that this was not the case. It is possible that there was some conjugation between A and B upon mixing that resulted in the formation of magnetically active microbubbles as in C(ii).

The invention claimed is:

1. A method of preparing a suspension of microbubbles for use in a carrier liquid, wherein the microbubbles have a gas core and a liquid shell, said liquid shell comprising magnetic nanoparticles, and wherein the method comprises the steps of:
   (a) determining a size of the shell relative to the gas core and an amount of the nanoparticles in the shell of a microbubble that satisfy the following conditions:
      (i) a force due to buoyancy ($F_{BW}$) of the microbubble in the carrier liquid is greater than a weight (W) of the microbubble;
      (ii) a magnetic force ($F_M$) on the microbubble due to a magnetic field applied to the carrier liquid is greater than a combination of the weight (W) and the force due to buoyancy ($F_{BW}$) of the microbubble;
      (iii) said magnetic force ($F_M$) on the microbubble is greater than a force due to viscous drag ($F_D$) on the microbubble due to flow of the carrier liquid; and
      (iv) a scattering cross section ($\sigma_{scat}$) of the microbubble to ultrasound allows the microbubble to be detectable and rupturable on exposure to ultrasound;
   (b) using the amount of nanoparticles in the shell and the relative size of the shell to the gas core of the microbubble to determine the amount of the magnetic nanoparticles and the amount of liquid for the shell needed to prepare a suspension of the microbubbles; and
   (c) preparing a suspension of the microbubbles using the amount of the magnetic nanoparticles and the amount of liquid for the shell needed to prepare the suspension.

2. A method according to claim 1, wherein the amount of the nanoparticles in the shell of the microbubble is determined as a volume fraction α of the magnetic nanoparticles suspended in the liquid shell.

3. A method according to claim 2, wherein the step of determining a volume fraction α of the magnetic nanoparticles in the liquid shell that satisfies the further condition:
   (i) $0 < \alpha < 0.2$.

4. A method according to claim 1, wherein condition (i) is represented by:

$$-1 < \frac{F_{BW} + W}{W} < 0,$$

and the force due to buoyancy ($F_{BW}$) of the microbubble in the carrier liquid is determined by the equation:

$$F_{BW} = \frac{4}{3}\pi g \rho_l R_2^3$$

And the weight (W) of the microbubble is determined by the equation:

$$W = -\frac{4}{3}\pi g [\rho_g R_1^3 + (R_2^3 - R_1^3)((1-\alpha)\rho_0 + \alpha\rho_{np})]$$

wherein g is the acceleration due to gravity, $\rho_l$ is the density of the carrier liquid, $R_2$ is the radius of the microbubble, $\rho_g$ is the density of the gas in the gas core, $R_1$ is the radius of the gas core, α is the volume fraction of the magnetic nanoparticles in the shell of the microbubble, $\rho_0$ is the density of the liquid in which the nanoparticles are suspended, and $\rho_{np}$ is the density of the magnetic nanoparticles.

5. A method according to claim 1, wherein the carrier liquid is one of water, a cell culture medium, human or animal blood, or human or animal lymph.

6. A method according to claim 1, wherein condition (ii) is represented by:

$$|F_M| > |F_{BW} + W|,$$

and the magnetic force ($F_M$) on the microbubble is determined by the equation:

$$F_M = -\frac{4\pi\chi(B \cdot \nabla)B\alpha(R_2^3 - R_1^3)}{3\mu_0}$$

wherein χ is the effective volumetric susceptibility of the magnetic nanoparticles suspended in the shell, B is the strength of the applied magnetic field, α is the volume fraction of the magnetic nanoparticles in the shell of the microbubble, $R_2$ is the radius of the microbubble, $R_1$ is the radius of the gas core and $\mu_0$ is the permeability of free space.

7. A method according to claim 6, wherein the magnetic force ($F_M$) of the microbubble is determined for an applied magnetic field B, where $120 \geq B \geq 0$ T.

8. A method according to claim 1, wherein condition (iii) is represented by:

$$|F_M| > |F_D|$$

And the force due to viscous drag ($F_D$) on the microbubble in the carrier liquid is determined by the equation:

$$F_D = \frac{u^2 C_D \pi R_{02}^2}{2};$$

where u is the flow velocity of the carrier liquid, $C_D$ is the drag coefficient, $R_{02}$ is the static radius of the microbubble, $\mu_l$ is the viscosity of the carrier liquid.

9. A method according to claim 8, wherein the force due to viscous drag ($F_D$) on the microbubble is determined for flow velocities u, where $20 \geq u \geq 0$ ms$^{-1}$.

10. A method according to claim 1, wherein condition (iv) is represented by:

$$\sigma_{scat} \geq \frac{4\pi\omega^4 \rho_l^2 R_{01}^6}{((k - m\omega^2)^2 + b^2\omega^2)};$$

where $m = \rho_l R_{01}^2$, $$b = 4\mu_l + \frac{3.6 \times 10^{-8}}{R_{01}} \text{ and } k = 3 \times 10^5 + \frac{0.24}{R_{01}};$$

and ω is the frequency of the ultrasound, $\rho_l$ is the density of the carrier liquid, $R_{01}$ is the initial radius of the gas core of the microbubble and $\mu_l$ is the viscosity of the carrier liquid.

11. A method according to claim 10, wherein the microbubble scattering cross section $\sigma_{scat}$ is determined for an ultrasound frequency $\omega$, where $\omega=2\pi f$ and $20 \geq f \geq 0.5$ MHz.

12. A method according to claim 1, wherein the amount of nanoparticles in the shell and the relative size of the shell to the gas core is determined using one or more of the following parameters:

$$\psi = \frac{F_{BW} + W}{W}, \text{ where } -1 > \psi > 0; \quad (1)$$

$$\varphi = \frac{F_M}{F_{BW} + W}, \text{ where } \varphi < -1; \text{ and} \quad (2)$$

$$\lambda = \frac{F_M}{|F_D|}, \text{ where } \lambda < -1. \quad (3)$$

13. A method according to claim 1, wherein the parameter $\xi$ represents the relative size of the shell to the gas core of a microbubble, where $$\xi = \frac{R_2}{R_1} - 1,$$

$R_2$ is the radius of the microbubble and $R_1$ is the radius of the gas core, and $\xi$ is not greater than 1.

14. A method according to claim 1, wherein step (a) of claim 1 includes determining the minimum relative size of the shell to the gas core of a microbubble, and/or includes determining the minimum amount of nanoparticles in the shell of a microbubble.

15. A method according to claim 1, wherein the step of preparing a suspension of the microbubbles comprises shaking and/or sonicating an aqueous solution comprising a material for coating the microbubble shell, the magnetic nanoparticles and the liquid for the shell, then, allowing the solution to settle before extracting a lower part of the solution.

16. A method according to claim 1, wherein the magnetic nanoparticles are ferromagnetic nanoparticles.

17. A method according to claim 1, wherein the average diameter of the magnetic nanoparticles is from 5 to 30 nm.

18. A method according to claim 1, wherein the gas core of the microbubble is selected from air, a noble gas, carbon dioxide, nitrogen, oxygen and mixtures thereof.

19. A method according to claim 1, wherein the liquid shell of the microbubble comprises a hydrocarbon oil.

20. A method according to claim 1, wherein an agent is added to the suspension of microbubbles, or is suspended in the liquid shell of the microbubble.

21. A suspension of microbubbles for use in a carrier liquid, wherein the microbubbles have a gas core and a liquid shell, said liquid shell comprising magnetic nanoparticles, and wherein substantially all of the microbubbles satisfy the following conditions:
   (i) a force due to buoyancy ($F_{BW}$) of the microbubble in the carrier liquid is greater than a weight (W) of the microbubble;
   (ii) a magnetic force ($F_M$) on the microbubble due to a magnetic field applied to the carrier liquid is greater than a combination of the weight (W) and the force due to buoyancy ($F_{BW}$) of the microbubble;
   (iii) said magnetic force ($F_M$) on the microbubble is greater than the force due to a viscous drag ($F_D$) on the microbubble due to flow of the carrier liquid; and
   (iv) a scattering cross section ($\sigma_{scat}$) of the microbubble to ultrasound allows the microbubble to be detectable and rupturable on exposure to ultrasound.

22. A suspension according to claim 21, wherein the diameter of the microbubbles is from 1 to 10 μm.

23. A suspension according to claim 21, wherein the suspension further comprises an agent, which is optionally suspended in the liquid shell of the microbubbles.

* * * * *